United States Patent [19]
Watts, III

[11] Patent Number: 6,108,608
[45] Date of Patent: Aug. 22, 2000

[54] METHOD OF ESTIMATING PROPERTIES OF A MULTI-COMPONENT FLUID USING PSEUDOCOMPONENTS

[75] Inventor: James W. Watts, III, Houston, Tex.

[73] Assignee: ExxonMobil Upstream Research Company, Houston, Tex.

[21] Appl. No.: 09/456,709

[22] Filed: Dec. 9, 1999

Related U.S. Application Data

[60] Provisional application No. 60/112,898, Dec. 18, 1998, and provisional application No. 60/165,353, Nov. 12, 1999.

[51] Int. Cl.$^7$ ..................................... G01F 23/00
[52] U.S. Cl. .............................. 702/30; 703/10
[58] Field of Search ................... 702/6, 12, 13, 702/22, 30; 73/61.41, 61.44; 703/2, 9, 10

[56] References Cited

U.S. PATENT DOCUMENTS

| | | | |
|---|---|---|---|
| 4,154,300 | 5/1979 | Vinatieri et al. | 166/252 |
| 5,710,726 | 1/1998 | Rowney et al. | 364/578 |

OTHER PUBLICATIONS

Acs, Gábor, Doleschall, Sándor, and Farkas, Éva. "General Purpose Compositional Model," *Society of Petroleum Engineers Journal*, (Aug. 1985) pp. 543–553.

Coats, Keith H. "Simulation of Gas Condensate Reservoir Performance," *Journal of Petroleum Technology*,(Oct. 1985) pp. 1870–1886.

Chaudhari, Narayan M. "An Improved Numerical Technique for Solving Multidimensional Miscible Displacement Equations," *Society of Petroleum Engineers Journal*, (Sep. 1971) pp. 277–284.

Taylor, A.J. "Computer Simulation of Gas Condensate Reservoirs," presentation at Condesate Reservoir Studies Seminar, London, England (Oct. 17, 1984)G1–G43.

Stamstaki, S. "A 4–Component Compositional Model Ternary and Quarternary Representation of Gas Condensate Systems," Society of Petroleum Engineers, SPE Technical Publications, Paper No. SPE 23409, (May 6, 1991) pp. 1–30.

Diamond, L. and Rondon, Cesar R. "Simulation Studies of Gas–Injection into Gas–Condensate Reservoirs," SPE Latin American Petroleum Engineering Conference, Rio de Janeiro (Oct. 16–18, 1990) Paper No. SPE 21060, pp. 1–13.

Goldthorpe, W.H. "Simulation of Gas Injection Processes in Gas–Condensate Reservoirs Using a Binary Pseudo–Component Representation," SPE Asia–Pacific COnference, Sydney, Australia (Sep. 13–15, 1989) Paper No. SPE 19470, pp. 45–54.

Leibovici, C.F., Govel, P.L., Piacentino, Thomas. "A Consistent Procedure for the Estimation of Pseudo–Component Properties," 68th Annual Technical Conference and Exhibition of the Society of Petroleum Engineers, Houston, Texas (Oct. 306, 1993) paper No. 26611, pp. 21–26.

(List continued on next page.)

*Primary Examiner*—Patrick Assouad
*Attorney, Agent, or Firm*—Gary D. Lawson

[57] ABSTRACT

Disclosed is a method for estimating properties of a multi-component fluid using pseudocomponents. The fluid is characterized using a set of base components and a set of fluid compositions is defined that corresponds to fluid compositions expected to occur in computations of interest. Pseudocomponents are defined to represent the multi-component fluid by (i) defining an ordered set of vectors corresponding to a characteristic of the base components, each vector containing one entry for each base component, the first vector being most representative of the set of compositions according to a predetermined criterion and each vector thereafter in the set being less representative of the set of compositions than the vector before it, and (ii) selecting a subset of the ordered set that comprises the first vector and a predetermined number of vectors immediately thereafter, the subset of vectors corresponding to a pseudocomponent characterization of the multi-component fluid.

22 Claims, 4 Drawing Sheets

OTHER PUBLICATIONS

Ariadinata, T.T., Sinegar, Septoratno and Hyas, Yusnal. "Gas Condesate Compositional Reservoir Simulation by Reducing the Number of Components into Pseudo Components into Pseudo Components," Proceedings Indonesian petroleum Association, Twenty Fourth Annual Convention (Oct. 1995) Paper No. IPA95-2.1-038, pp. 103–111.

Joergensen, M. and Stenby, E.H. "Optimization of Pseudo–component Selection for Compositional Studies of Reservoir Fluids," 70th Annual Technical Conference and Exhibition, Dallas, Texas (Oct. 22–25, 1995) Paper No. SPE 30789, pp. 917–927.

Bennion, D.W.; Bennion, D.B.; Thomas, F.B; and Shaw, D.R. "Compositional Numerical Modelling in Naturally Fractured Reserviors," 47th Annual Technical Meeting of The Petroleum Society, Calgary, Alberta, Canada (Jun. 10–12, 1996) pp. 1–12.

Verdiére, Sophie. "Dual Mesh Method for Efficient Multiphase Flow Simulations in Heterogeneous Reservoirs," 1997 SPE Annual Technical COnference and Exhibition, San Antonio, Texas (Oct. 5–8, 1997) pp. 579–590.

Golub, G. and Kahan, W. "Calculating the Singular Values and Pseudo–Inverse of a Matrix," *J. Siam Numer. Anal.*, Ser. B, vol. 2, No. 2 (1966) pp. 205–224.

Montel, F. and Gouel, P.L. "A New Lumping Scheme of Analytical Data for Compositional Studies," 59th Annual SPE Technical Conference and Exhibition, Houston, Texas (Sep. 16–19, 1984) Paper No. SPE 13119, pp. 1–13.

Newley, T.M.J. and Merrill Jr., R.C. "Pseudocomponent Selection for Compositional Simulation," 64th Annual Technical Conference and exhibition of the Society of Petroleum Engineers, San Antonio, Texas (Oct. 8–11, 1989) Paper No. SPE 19638, pp. 1–9.

Mehra, Rakesh K.; Heidemann, Robert A.; Aziz, Khalid; Donnelly, John K. "A Statistical Approach for Combining Reservoir Fluids into Pseudo Components for Compositional Model Studies,"57th Annual Fall Technical Conference and Exhibition of the Society of petroleum Engineers of AIME, New Orleans, LA (Sep. 26–29, 1982) Paper No. SPE 11201, pp. 1–11.

Hong, K.C. "Lumped–Component Characterization of Crude Oils for Compositional Simulational," 1982 SPE/DOE Third Joint Symposium on Enhanced Oils Recovery of the Socity of Petroleum Engineers, Tulsa, OK (Apr.4–7, 1982) Paper No. SPE/DOE 10691, pp. 1–13.

Leibovici, Claude F.; Barker, John W.; and Waché, David. "A Method for Delumping the Results of a Compositional Reservoir Simulation," SPE Proceedings, 1998 SPE Annual Technical Conference and Exhibit, New Orleans, LA (Sep. 27–30, 1998) Paper No. SPE 469068, pp. 1–30.

METHOD OF ESTIMATING PROPERTIES OF A MULTI-COMPONENT FLUID USING PSEUDOCOMPONENTS

This application claims the benefit of U.S. Provisional Application No. 60/112,898 filed Dec. 18, 1998 and U.S. Provisional Application No. 60/165,353 filed Nov. 12, 1999.

FIELD OF THE INVENTION

The invention relates generally to a method for estimating properties and/or behavior of a multi-component fluid in one or more volumetric zones using a pseudocomponent representation of the multi-component fluid. The method is particularly useful in estimating properties and/or behavior of fluids contained in hydrocarbon-bearing, subterranean formations or in hydrocarbon processing facilities.

BACKGROUND OF THE INVENTION

Reservoir simulation is a process of inferring the behavior of a real reservoir from the performance of a model of that reservoir. Because mass transfer and fluid flow processes in petroleum reservoirs are so complex, reservoir simulations can only be done using computers. Computer programs that perform calculations to simulate reservoirs are called reservoir simulators. The objective of reservoir simulation is to understand the complex chemical, physical, and fluid flow processes occurring in a petroleum reservoir sufficiently well to be able to predict future behavior of a reservoir and to maximize recovery of hydrocarbons. The reservoir simulator can solve reservoir problems that are not solvable in any other way. For example, a reservoir simulator can predict the consequences of reservoir management decisions.

Reservoir simulation typically refers to the hydrodynamics of flow within a reservoir, but in a larger sense it also refers to the total petroleum system which includes the reservoir, the surface facilities, and any interrelated significant activity.

Compositional reservoir simulations are used to simulate recovery processes for which there is a need to know the compositional changes in at least part of the reservoir. For example, compositional simulations can be helpful in studying (1) depletion of a volatile oil or gas condensate reservoir where phase compositions and properties vary significantly with pressure below bubble or dew point pressures, (2) injection of non-equilibrium gas (dry or enriched) into a black-oil reservoir to mobilize oil by vaporization into a more mobile gas phase or by condensation through an outright (single-contact) or dynamic (multiple-contact) miscibility, and (3) injection of $CO_2$ into an oil reservoir to mobilize oil by miscible displacement and by oil viscosity reduction and oil swelling.

The compositional model describes reservoir hydrocarbon content as a multiple-component mixture. Gas/oil phase properties and equilibrium are calculated from pressure and composition dependent correlations or more typically from a suitable equation of state (EOS). Several EOSs have been developed and are in use today, including for example the Redlich-Kwong EOS and the Peng-Robinson EOS.

Compositional reservoir simulators using an EOS to describe the phase behavior of multi-component fluid mixtures are expensive to use because of the large number of iterative phase equilibrium calculations and large computer storage space required. The number of equations having to be solved in EOS calculations is proportional to the number of components in the fluid. Since a reservoir fluid can contain hundreds of pure components, it is not economically practical to perform compositional simulations in which all reservoir components are used in the calculations. It is therefore desirable to keep the number of components used in describing a fluid mixture to a minimum.

To limit the computational time of compositional reservoir simulations, a common practice is to pseudoize the fluid description. In the pseudoization, the pure compounds are grouped into a number of component groups, termed pseudocomponents. The pseudocomponents are treated as if they were pure components in subsequent reservoir simulations.

It is obvious that the pseudoization can lead to losses in accuracy and flexibility in the equation of state calculations. The accuracy depends both on how the pseudocomponents are developed and the number of pseudocomponents. The number of pseudocomponents used in a study will usually represent a compromise between accuracy and computational cost. Therefore, considerable effort has been made to formulating pseudoization methods in which the fluids can be described as accurately as possible, with as few pseudocomponents as possible.

Many different methods have been proposed for selecting pseudocomponents. The methods include (1) ordering the original components of the fluid with respect to their normal boiling point, and grouping the original components to form pseudocomponents with approximately equal mole fractions, (2) grouping the original components to form pseudocomponents having approximately equal weight fractions, (3) grouping the pure components with similar properties by an iterative scheme in which the distances between the pure components and the pseudocomponents is minimized, (4) selecting pseudocomponents based on molar averaging of the pure component properties, and (5) grouping components using weight-based averaging of the pure component properties.

In these pseudoization methods, the pseudocomponents are formed by "lumping." Each lumped pseudocomponent contains only a few "base" components, and each base component appears in only one pseudocomponent. These methods work reasonably well for performing simulation computations. However, the pseudoization methods do not directly provide an effective way to "delump" the results. Delumping involves converting the computed results expressed in terms of pseudocomponents back to an expression in terms of the original base components. Several approaches to delumping have been proposed, most of which perform supplementary computations after the simulation has been completed. Some involve delumping only the results of interest, while others require performing computations at all gridblocks for all simulation timesteps.

A pseudoization method that is capable of being delumped can be important in modeling fluid flow between two zones having different fluid characteristics. This delumping capability can be particularly useful in estimating fluid properties of surface processing facilities, which often requires a detailed fluid representation. A few (for example, three to eight) pseudocomponents may be adequate for most reservoir computations, while many more pseudocomponents may be needed to adequately represent a processing facility. In modeling a reservoir and a processing facility, the model in effect comprises two fluid representation regions—the reservoir and the processing facilities—each requiring a different level of detail in its fluid representation. Often it would be desirable to divide the reservoir into similar fluid representation regions. In many reservoir models, significant changes and complex behavior occur in only one part of the model. A larger number of pseudocomponents could be used in one zone and a smaller number in another zone where such behavior does not occur. This would require converting any fluid that crosses a boundary between these different types of zones from one representation to another. Pseudoization methods proposed in the past have not been able to effectively estimate fluid behavior and properties as the fluid flows between such zones.

A need exists for an improved method for developing pseudocomponents that can effectively represent a multi-component fluid in a reservoir and a pseudoization method that can effectively transform a fluid as it flows between regions of a reservoir having different fluid representations.

SUMMARY

This invention relates to a method for estimating one or more properties of a multi-component fluid contained in at least one volumetric zone. The first step characterizes the multi-component fluid using a set of base components. A set of fluid compositions is then defined that corresponds to fluid compositions predicted to occur in the volumetric zone. One or more pseudocomponents are then defined to represent the multi-component fluid by the following sequence of steps:
  (i) defining an ordered set of vectors corresponding to a characteristic of said base components, each vector containing one entry for each base component, the first vector of the ordered set being most representative of the set of compositions according to a predetermined criterion and each vector thereafter in the ordered set being less representative of the set of compositions than the vector before it; and
  (ii) selecting a subset of said ordered set of vectors, said subset comprising the first vector and a predetermined number of vectors immediately thereafter, said subset of vectors corresponding to a pseudocomponent characterization of the multi-component fluid.

The subset of vectors is then used to estimate one or more properties of said multi-component composition.

In one embodiment, the steps of defining the pseudocomponents further comprise determining, for each vector of the subset of vectors, a dominant component corresponding to a predetermined criterion, and modifying each selected vector by eliminating all other selected vectors' dominant components. Each modified vector is then normalized. In another embodiment, once the dominant components are known, the pseudocomponents are defined by normalizing the vectors obtained in a least squares calculation.

In still another embodiment of this invention, properties of a multi-component fluid are estimated as the fluid crosses a boundary between a first region and a second region, each region having a different pseudocomponent representation. In this embodiment, the pseudocomponent representation of the fluid in one region is transformed to a base component representation and the base component representation is transformed to the pseudocomponent representation in the second region.

DETAILED DESCRIPTION OF THE PREFERRED EMBODIMENTS

Figure 1:
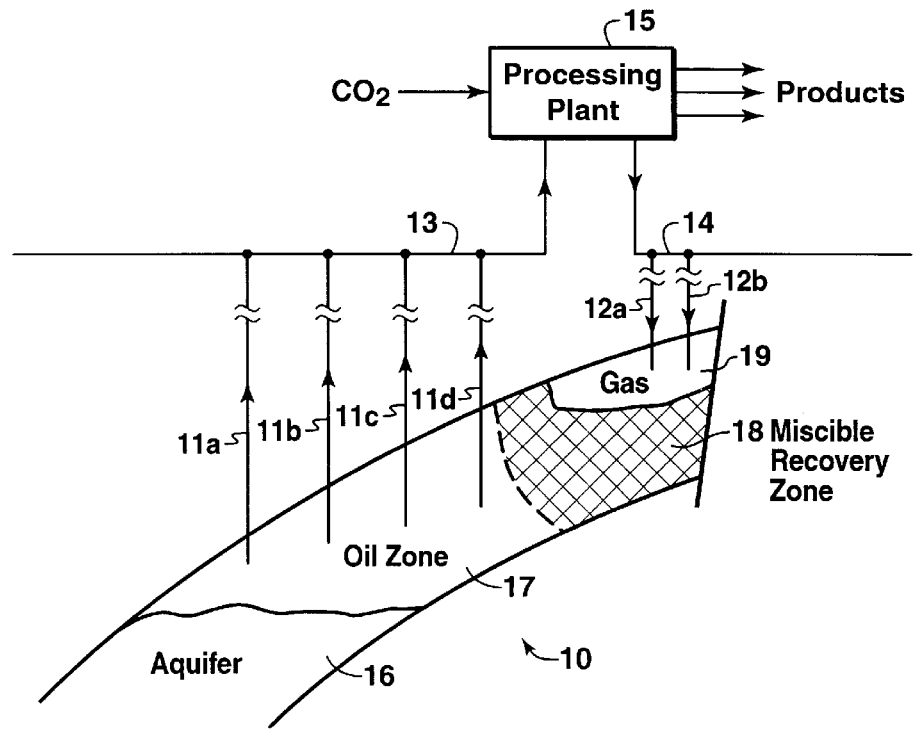
FIG. 1 is an illustrational view of a subterranean hydrocarbon-bearing reservoir having production wells and injection wells that are connected to a processing plant, all of which can contain fluids the properties of which can be estimated in accordance with the method of this invention.

The following description makes use of a several mathematical symbols, many of which are defined as they occur in this description. Additionally, for purposes of completeness, a symbols table containing definitions of symbols used herein is presented following the detailed description.

Definitions

Before proceeding with the detailed description, definitions of principal terms used in the description is provided to aid the reader in understanding the invention.

Fluid Characterization means a mathematical representation of a set of fluids that mimics their important behavior at the compositions, pressures, and temperatures encountered in a reservoir or facility being simulated. The fluid characterization will typically comprise (1) a set of either pure components or pseudocomponents, (2) an equation of state such as the Peng-Robinson equation of state and its associated parameters, and (3) physical relationships or correlations used for computing certain fluid properties.

Base Characterization means a fluid characterization determined by selecting a set of components and tuning (or matching) physical parameters to provide a match of desired behavior for the conditions of interest, typically performed by matching available laboratory data.

Base Component means a component used in the base fluid characterization. Many base components will be hydrocarbon species such as methane, ethane, propane, butane, and heavier hydrocarbons. Some can be mixtures of multiple components, such as $C_{7+}$, $C_{10-12}$, $C_{20+}$, etc and may also include, for example, carbon dioxide, nitrogen, and hydrogen sulfide. The base components typically range from 10 to 50.

Pseudocomponent means a fluid mixture used to reduce the cost of performing reservoir and facility computations. Each pseudocomponent comprises a fixed mixture of base components.

Pseudocomponent Characterization means fluid characterization that uses a set of pseudocomponents with physical parameters computed from the base characterization's parameters. The number of pseudocomponents will be smaller than the number of base components.

Base Composition means a fluid composition expressed in terms of the amount of each base component per unit amount of fluid present.

Pseudocomponent Composition means a fluid composition expressed in terms of the amount of each pseudocomponent per unit amount of fluid present.

Base Representation means a representation of a fluid in terms of the amount of each base component present.

Pseudocomponent Representation means a representation of a fluid in terms of the amount of each pseudocomponent present.

This invention relates to a method for estimating fluid properties of a multi-component fluid contained in one or more volumetric zones. The volumetric zones could be different zones in a hydrocarbon-bearing, subterranean reservoir, and they may also comprise injection wells, production wells, above-ground fluid gathering facilities, flowlines, and fluid processing facilities of chemical plants, refineries, and gas plants.

The inventor has discovered a new method for representing a multi-component fluid system using pseudocomponents derived by a mathematical technique, with the pseudocomponents corresponding to a set of base compositions. In one embodiment of this invention, each pseudocomponent can contain all the base components except that a dominant base component, selected by a predetermined selection criterion, appears in only the pseudocomponent for which it is the dominant component. Once the pseudocomponent is determined, the fugacity of its dominant component is used as the pseudocomponent's fugacity in phase equilibrium calculations, assuming that equilibrium calculations are being performed based on equality of fugacities. If equilibrium calculations are being performed in some other way, a corresponding approach may be used, adapted to the particulars of how the equilibrium calculations are being performed. For example, if equilibrium ratios (K-values) are used, the pseudocomponent's equilibrium ratio is assumed to be the same as its dominant component's equilibrium ratio.

The pseudocomponents generated by the practice of this invention always have the same definition for a given model, regardless of the phase or phases that contain the pseudocomponents. By defining pseudocomponents in accordance with this invention, a fluid can be modeled as it crosses a boundary between two regions having different pseudocomponent representations. The pseudocomponent representation in one region is transformed to a base representation and the base representation is transformed to the pseudocomponent representation in the other region. FIG. 1 illustrates examples of regions that typically require different fluid representations.

FIG. 1 is a simplified, two-dimensional, section of a producing oil reservoir 10 with a schematic depiction of production wells 11a, 11b, 11c, and 11d, injection wells 12a and 12b, flow lines 13 and 14, and surface processing plant 15. The oil zone 17 contains water as well as oil, and the oil in the oil zone 17 contains gas held in solution by the typically high reservoir pressure. As a result, the four production wells (11a–d) produce oil primarily, but they also produce varying amounts of water and gas. The production streams are combined and sent by flowline 13 to the processing plant 15, which separates water from the produced hydrocarbons and also separates the hydrocarbons into three product streams—gas, oil, and natural gas liquids (NGLs). The processing plant 15 can also take in carbon dioxide from an external source, combine it with some of the produced gas and NGLs, and send the gas mixture through distribution line 14 to the injection wells 12a and 12b. This injected gas mixture 19, at reservoir temperature and pressure, will displace oil miscibly, making it possible to recover a high fraction of the oil in the contacted area. In addition, there is an aquifer 16 from which water flows into the reservoir as the reservoir pressure declines.

A reservoir simulation model of the reservoir 10 can be divided into multiple regions with different pseudocomponent characterizations for each region. Having multiple pseudocomponent characterizations is often desirable because some parts of the model require more detailed fluid representation than other parts. The simplest pseudocomponent characterization would typically be the aquifer 16. The aquifer starts out containing no hydrocarbons, but as the reservoir 10 is exploited it is possible for small amounts of hydrocarbon to be pushed down into the aquifer 16. As the hydrocarbons move into the aquifer they will typically be trapped as residual saturation and will be unable to move further. As a result, it is not necessary to represent these hydrocarbons accurately. Merely recognizing their presence and the volume that they occupy is adequate. This can be done with a single hydrocarbon pseudocomponent for aquifer 16. The oil zone 17 requires a somewhat more accurate representation. Since it contains both oil and gas, it is typically represented by at least two pseudocomponents. However, in the oil zone little is happening other than movement of oil and the gas it contains to the production wells 11a–d. This will not lead to wide variations in composition, and two pseudocomponents would typically be adequate. This is not true in the miscible recovery zone 18 in which a new component, carbon dioxide, is present. Also, a continuous composition path is traversed as the injected gas mixture 19 miscibly displaces the inplace oil. Several pseudocomponents, typically five to ten, would be needed to obtain the desired accuracy to estimate fluid properties and behavior in the miscible recovery zone 18. In the processing plant 15, a variety of processes take place and the fluids being processed undergo a wider range of pressure and temperature than are encountered in the reservoir. The plant's processes typically occur at pressures much lower than those in the reservoir. A much more detailed fluid representation, and therefore significantly more pseudocomponents, would be needed to estimate fluid behavior and properties in the processing plant than would be need to estimate fluid behavior in the reservoir 10.

Although the primary focus of compositional reservoir simulation concerns fluid properties and behavior within a subterranean reservoir, the method of this invention can be used in estimating fluid properties in non-reservoir fluid media such as wellbore tubing, surface flow lines, pipelines, separators, and other facilities such as oil and gas processing plants and refineries.

In this description of the invention, the pseudoization method will be applied to a reservoir generally illustrated in FIG. 1. The reservoir is treated as a group of volume cells or gridcells. Typically these are defined so as to permit flow in three dimensions, but optionally simpler one- or two-dimensional models can also be used. The art of reservoir simulation using either compositional or black-oil representations of the hydrocarbons is well established. The units within the processing plant 15, the flow lines 13 and 14, and the wells 11a–d and 12a–b may be modeled as nodes and connections or they may be modeled in any other suitable way by modeling techniques well known in the art. Regardless of how the facilities are modeled, flow stream compositions and flow rates are required.

The first general step in applying the pseudoization method of this invention to a reservoir generally illustrated in FIG. 1 is to characterize the hydrocarbon fluids in terms of a set of base components. The first step in doing this is to decide how many base components to use and to define the individual base components. This characterization is preferably done using measurements made in the laboratory on fluid samples taken from the reservoir. The number of components varies, with numbers in the range 10 to 40 being typical. The next step is to tune a suitable equation of state and/or other physical parameters to enable the fluid characterization to match available laboratory measurements. This two-step process may be iteratively repeated until a characterization is obtained that is within desired limits of accuracy or acceptability. Processes for characterizing multicomponent fluids in terms of base components are well known in the art. The characterization defined in terms of the base components is referred to in this description as the base characterization.

An additional initial step is to define a volumetric zone or zones to be modeled and to equate the volumetric zone or zones being modeled to a volumetric system comprising a plurality of volume cells or gridcells. The practice of this invention is not limited to any particular type or size of gridcells. The gridcells may be of any geometric shape, such as parallelepipeds (or cubes) or hexahedrons (having four vertical corner edges which may vary in length), or tetrahedrons, rhomboids, trapezoids, or triangles. The grid may comprise rectangular cells organized in a regular, structured fashion, or it may comprise cells having a variety of shapes laid out in an irregular, unstructured fashion. The gridcells will be developed to model the reservoir and its associated wells and facilities. Development of such suitable gridcells for modeling the various zones are known to those skilled in the art.

The next step in practicing this invention is to divide the model into computational regions, each of which can use a different pseudocomponent characterization. Although this invention is not limited to the number of computational regions that may be modeled, the number of regions having different pseudocomponent characterizations will typically not exceed about five.

To conserve computational resources, it is desirable as an optional step to construct one or more simplified models that exhibit the important behavior of the detailed model. This simplified model could, for example, contain only a few hundred gridcells instead of the few hundred thousand gridcells to be used in the final model, and it could contain only a few representative wells and facilities. This simplified model could correspond to the entire detailed model, or a separate simplified model could be developed for each computational region, or multiple models could be developed to yield behavior characteristics of a given computational region. The simplified model or models should generate compositions that span the range of compositions expected in the computations of interest, and they should be designed with this in mind. One skilled in the art of compositional reservoir simulation would be able to design such simplified models. Modeling packages that can aid in constructing such simplified models are commercially available and are known to those skilled in the art.

Once the fluid has been characterized in terms of a set of base components, the next step is to define a set of base compositions corresponding to fluid compositions predicted to occur in the regions being modeled. The base compositions are preferably obtained by performing computations on the simplified model or models using the base characterization. The set of base compositions will preferably contain more compositions than there are base components, and more preferably the set will contain several times as many compositions as base components.

The next step is to define an ordered set of vectors corresponding to a characteristic of the base components, with each vector containing one entry for each base component. The first vector of the ordered set is most representative of the set of base compositions according to a predetermined criterion, for example compositions can be expressed in mole fractions, and each vector thereafter in the order is less representative of the set of compositions than the vector before it. This is carried out by assembling the set of base compositions into a matrix, each row of which is one of the base compositions, then determining a set of vectors, fewer in number than the base components, that when appropriately combined can best reproduce the rows of this matrix. This set of vectors is determined using singular value decomposition, with the right singular vectors produced by singular value decomposition being the desired vectors. The desired pseudocomponents will be based on a subset of these right singular vectors. The subset will comprise the first of the right singular vectors, one singular vector for each pseudocomponent. The subset will normally comprise 3 to 10 right singular vectors. For example, if three pseudocomponents are to be used, the three pseudocomponents will be based on the first three right singular vectors. Vector determinations used in the practice of this invention can be performed by those skilled in the art in light of the teachings of this description. For examples of vector calculations see (1) a paper by G. Golub and W. Kahan, "Calculating the Singular Values and Pseudo-inverse of a Matrix," *SIAM Journal of Numerical Analysis* (May 1965) 205–224 and (2) a book by William H. Press, Saul A. Teukolsky, William T. Vetterling, and Brian P. Flannery, *Numerical Recipes,* Second Edition, Cambridge University Press (1994).

The next step is to decide how many pseudocomponents to use in each computational region. The singular values provide a measure of how accurately a given number of right singular vectors can approximate the rows of the matrix and can be used as a guide in making this decision. The final decision will be based on how accurately a pseudocomponent characterization reproduces the results using the computations of interest when compared to the results of using the base characterization in the same computations.

Once the desired number of pseudocomponents has been selected, the right singular vectors are converted to pseudocomponents. Beginning with the first right singular vector, the vectors are converted one by one until the desired predetermined number of pseudocomponents is obtained. Once the pseudocomponents have been defined, their equation of state and other characterization parameters can be determined directly from the base fluid characterization. Moreover, as discussed in more detail below, because the pseudocomponent compositions have been defined to match the compositions of interest, base compositions can be computed with acceptable accuracy from the pseudocomponent compositions. From the base compositions, fluid properties such as molecular weight, density, and viscosity can be computed. However, with some multi-component fluids, these desired properties may be obtained with sufficient accuracy using only the pseudocomponent composition, without computing the base composition.

In one embodiment of this invention, the next step is to select for each vector, the vector's dominant component. A determination based on mole fraction is one of several possible criteria for defining the dominant component. The component having the largest mole fraction, at the time of selection, becomes the dominant component for that vector.

Consider as a non-limiting example determining three pseudocomponents for a five base-component system. The process begins with the three most significant right singular vectors. These vectors can be assembled into a matrix, the transpose of which is $$v^T = \begin{bmatrix} v_{11} & v_{21} & v_{31} & v_{41} & v_{51} \\ v_{12} & v_{22} & v_{32} & v_{42} & v_{52} \\ v_{13} & v_{23} & v_{33} & v_{43} & v_{53} \end{bmatrix} \quad (1)$$

The first row in this matrix is the most significant right singular vector, the second is the second most significant, and so on. Assume that the largest entry in the first row is $v_{11}$. Then the first component will become the corresponding pseudocomponent's dominant component. The first entry is eliminated from the second and third rows using a process similar to Gaussian elimination. The first row is multiplied by $v_{12}/v_{11}$ and subtracted from the second. Similarly, the first row is multiplied by $v_{13}/v_{11}$ and subtracted from the third. The result is a matrix of intermediate vectors of the following form.

$$v_{iI}^T = \begin{bmatrix} v_{11} & v_{21} & v_{31} & v_{41} & v_{51} \\ 0 & v_{22} - \frac{v_{12}v_{21}}{v_{11}} & v_{32} - \frac{v_{12}v_{31}}{v_{11}} & v_{42} - \frac{v_{12}v_{41}}{v_{11}} & v_{52} - \frac{v_{12}v_{51}}{v_{11}} \\ 0 & v_{23} - \frac{v_{13}v_{21}}{v_{11}} & v_{33} - \frac{v_{13}v_{31}}{v_{11}} & v_{43} - \frac{v_{13}v_{41}}{v_{11}} & v_{53} - \frac{v_{13}v_{51}}{v_{11}} \end{bmatrix} \quad (2)$$

Next, the largest remaining element in the second row is determined, and the process is repeated. Finally, the largest element remaining in the third row is determined, and the process is repeated again. Assuming that component five is the second dominant component and component three is the third, the final matrix of intermediate vectors has the following general form, where d denotes the dominant component and x denotes a non-zero term.

$$v_{i3}^T = \begin{bmatrix} d & x & 0 & x & 0 \\ 0 & x & 0 & x & d \\ 0 & x & d & x & 0 \end{bmatrix} \quad (3)$$

Figure 2:
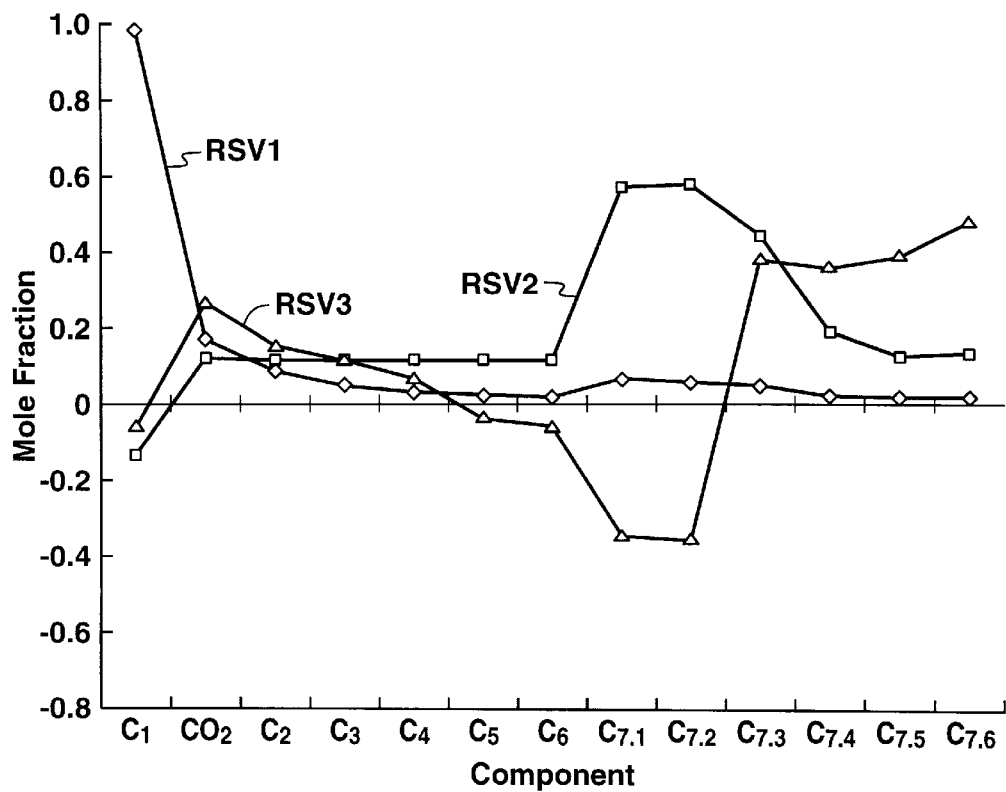
FIG. 2 illustrates in graphical form the first three right singular vectors, depicting the mole fraction of each component for a 13-component example of a pseudoization method of this invention.
Figure 3:
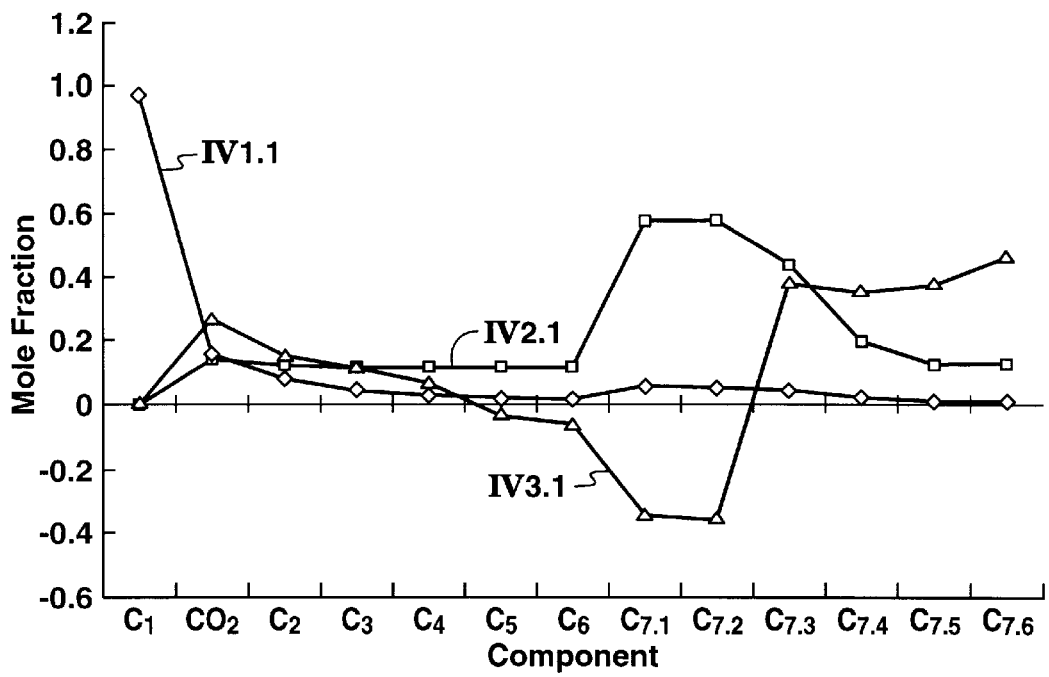
FIG. 3 illustrates in graphical form the first step of determining intermediate vectors for the 13-component example of FIG. 2.
Figure 4:
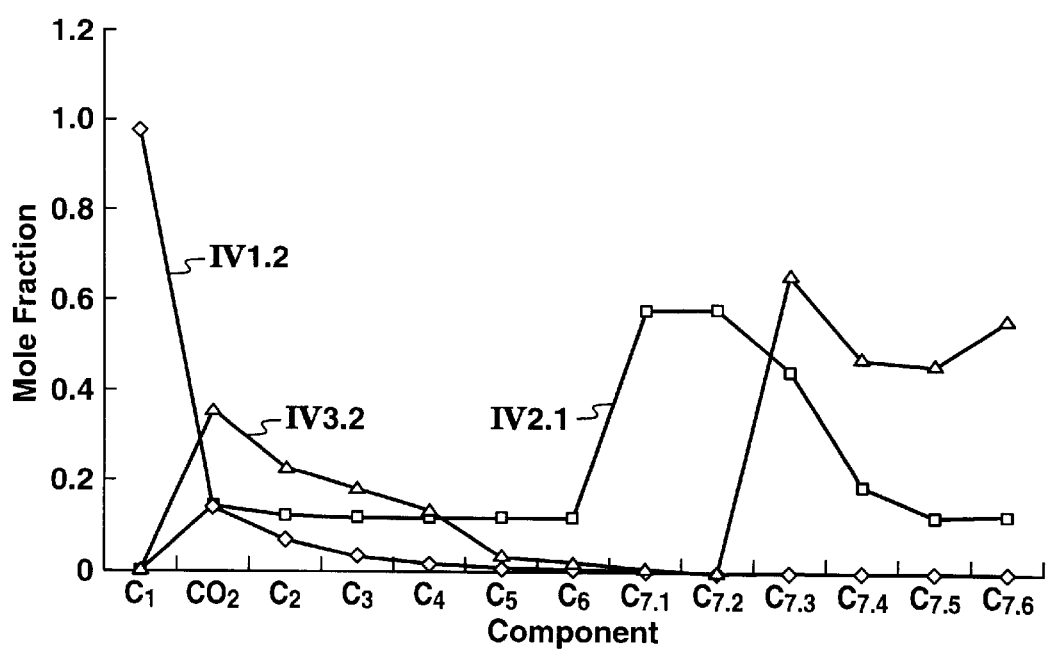
FIG. 4 illustrates in graphical form the second step of determining intermediate vectors for the 13-component example of FIG. 2.
Figure 5:
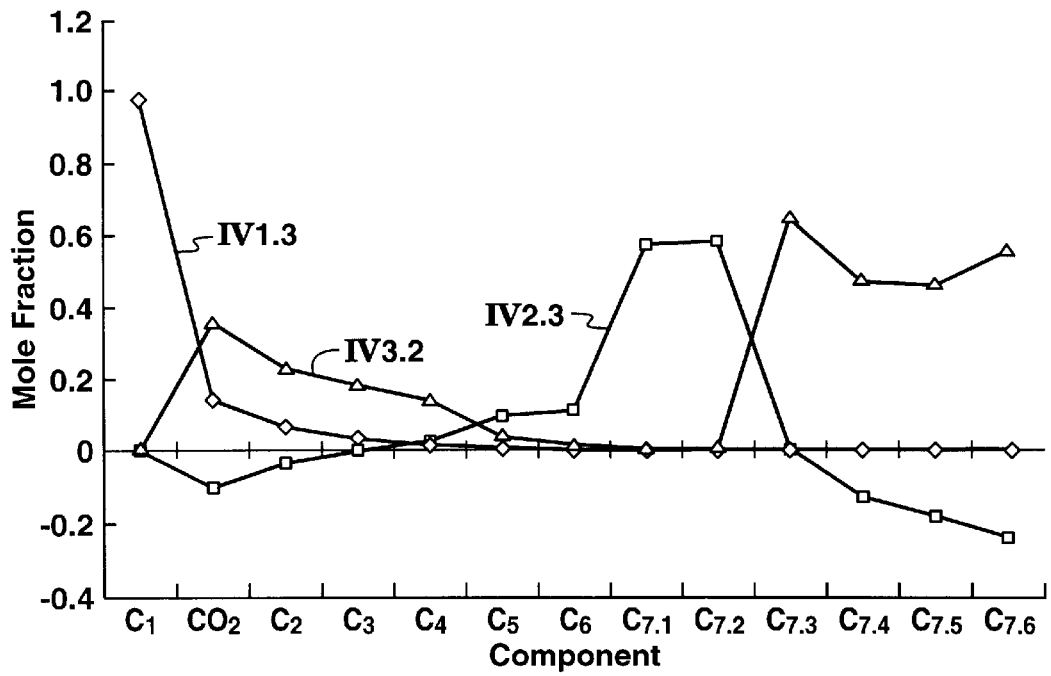
FIG. 5 illustrates in graphical form the third step of determining intermediate vectors for the 13-component example of FIG. 2.

FIG. 2 illustrates the first three right singular vectors determined for a 13-component system used in the example presented below. In FIG. 2, lines designated RSV1, RSV2, and RSV3 represent the first, second, and third singular vectors, respectively. Referring to RSV1 in FIG. 2, the dominant component for the first pseudocomponent is $C_1$. Its mole fraction is eliminated from each of the other vectors. FIG. 3 shows the result of this computation for the first three vectors. In FIG. 3, lines designated IV1.1, IV2.1, and IV3.1 represent intermediate vectors corresponding to RSV1, RSV2, and RSV3 of FIG. 2, respectively. In FIG. 3, note that the mole fraction of $C_1$, the first pseudocomponent's dominant component, in intermediate vectors IV2.1 and IV3.1 is zero. Following the same procedure beginning with intermediate vector IV2.1, the dominant component is $C_{7.2}$ (see FIG. 3). This component is eliminated from the other intermediate vectors (IV1.1 and IV3.1). FIG. 4 shows the result, with lines IV1.2, IV2.1, and IV3.2 corresponding to IV1.1, IV2.1, and IV3.1 of FIG. 3. Following the same procedure beginning with intermediate vector IV3.2, the dominant component for the third pseudocomponent is $C_{7.3}$ (see IV3.2 of FIG. 4). This component is eliminated from the other vectors. FIG. 5 shows the result, where IV1.3, IV2.3 and IV3.2 correspond to IV1.2, IV2.1 and IV3.2 of FIG. 4.

Figure 6:
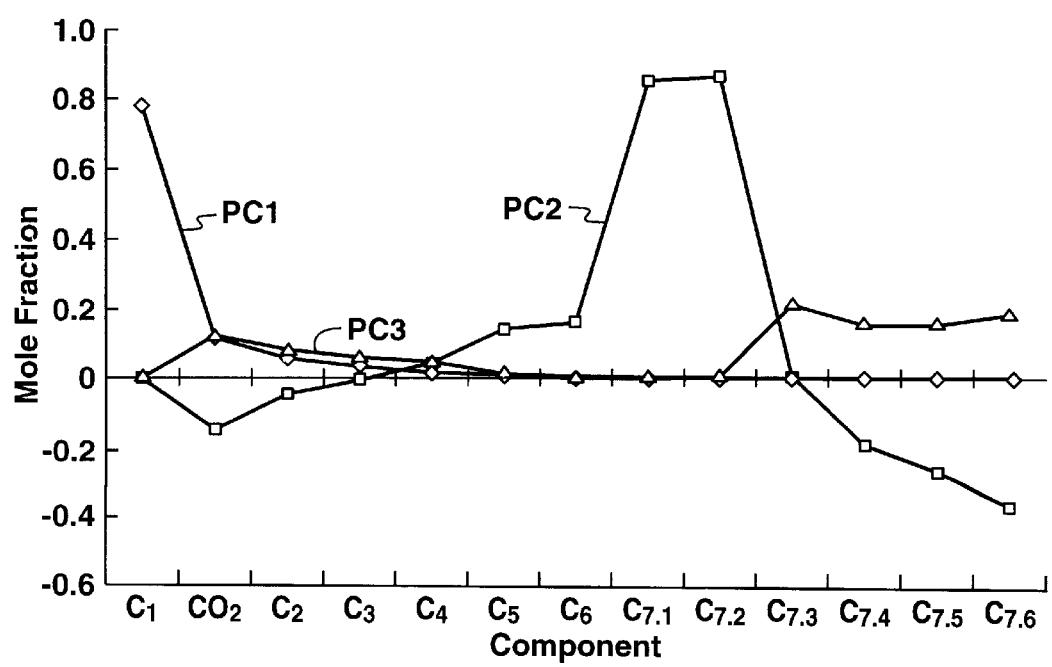
FIG. 6 illustrates three pseudocomponents for the 13-component example of FIG. 2.

Assuming that three pseudocomponents are to be used, the final computation is to normalize the intermediate vectors such that their defining mole fractions sum to unity. This is done for each intermediate vector by dividing each of its defining mole fractions by the sum of its defining mole fractions. The result is the three pseudocomponents shown in FIG. 6 where lines PC1, PC2, and PC3 represent the first, second, and third pseudocomponents, respectively.

It is desired that the dominant component be the one that best represents the pseudocomponent as a whole in phase equilibrium calculations. Typically, a good choice will be the component having the largest mole fraction in the pseudocomponent definition. As a result, one embodiment of this invention selects the component having the largest mole fraction at the time the pseudocomponent's dominant component is selected. Other criteria could be used. For example, modifications to a pseudocomponent made after its dominant component has been selected can result in a component other than its dominant component coming to have the largest mole fraction. These modifications occur as less significant pseudocomponents' dominant components are eliminated from the pseudocomponent of interest. If this occurs, the pseudocomponent determination process can be repeated, beginning with the pseudocomponent of interest, with a revised selection for the pseudocomponent's dominant component. Also, it is possible to use a more complex procedure, such as determining the correlation of each component's mole fraction with the optimal pseudocomponent mole fraction in a set of compositions, with the component having the highest correlation being selected as the dominant component. The additional complexity does not seem to be justified.

Once the dominant components are known, another way to determine an equivalent and similar set of pseudocomponents is to use least squares minimization. The approach is to determine the linear combination of dominant component concentrations that provides the best fit of the observed compositions. This is done component by component for each component that is not a dominant component.

Let $x_{obc}$ be the concentration of base component c (not a dominant component) in observation o. Then approximate $x_{obc}$ by $\hat{x}_{obc}$ where $$\hat{x}_{obc} = \sum_p a_{pc} x_{obd_p} \quad (4)$$

Here p denotes the pseudocomponent, $\alpha_{pc}$ is a constant to be determined through minimization of least squares, and $x_{obd_p}$ is the concentration of the $p^{th}$ pseudocomponent's dominant component in observation o. Define F as the sum over the observations of the squares of the errors in representing $x_{obc}$. Then $$F = \sum_o (\hat{x}_{obc} - x_{obc})^2 = \sum_o \left( \sum_p a_{pc} x_{obd_p} \right)^2 \quad (5)$$

Taking the derivative of F with respect to $\alpha_{qc}$, where q denotes a pseudocomponent, yields the condition for minimum least squares.

$$\sum_o \sum_p a_{pc} x_{obd_p} x_{obd_q} = \sum_o x_{obc} x_{obd_q} \qquad (6)$$

where $x_{obd_q}$ is the observed concentration of the $q^{th}$ pseudocomponent's dominant component. Eq. (3) yields an $N_{PC}$ by $N_{PC}$ set of equations, where $N_{PC}$ is the number of pseudocomponents. This set of equations is solved for the $\alpha_{pc}$. In this way, $\alpha_{pc}$ can be determined for all c corresponding to non-dominant components. The resulting unnormalized definition of pseudocomponent p is a vector containing the $\alpha_{pc}$ in the positions corresponding to non-dominant components, zeroes in positions corresponding to dominant components of pseudocomponents other than the $p^{th}$, and a one in the position corresponding to the $p^{th}$ pseudocomponent's dominant component. The final pseudocomponent definition is obtained by scaling the entries in this vector so that they sum to one.

A similar procedure can be used to "delump" lumped pseudocomponent fluid representations. Let $x_o$ be the concentration of lumped pseudocomponent in observation o. Then a perfect concentration of lumped pseudocomponent in observation o is given by $$x_{ol} = \sum_{c \in l} x_{obc} \qquad (7)$$

The concentration of base component c in observation o is approximated as a linear combination of these lumped pseudocomponent concentrations.

$$\hat{x}_{obc} = \sum_l a_{lc} x_{ol} \qquad (8)$$

Since there are no dominant components, c must range over all components. The least squares optimal values of $\alpha_c$ are determined by minimizing $$F = \sum_o (\hat{x}_{obc} - x_{obc})^2 = \sum_o \left( \sum_p a_{lc} x_{ol} - x_{obc} \right)^2 \qquad (9)$$

The $\alpha_c$ care determined by solving the set of equations $$\sum_o \sum_l a_{lc} x_{ol} x_{on} = \sum_o x_{obc} x_{on} \qquad (10)$$

where n denotes a lumped pseudocomponent. Given the $\alpha_c$, the "delumping" is performed by computing approximate base concentrations using equation (8).

After the pseudocomponents are known for each computational region, transformation matrices must be determined if there will be more than one computational region. There must be a transformation matrix for any flow from one computational region to another. If flow between two computational regions can only be in one direction, only one transformation matrix is needed for the computational region pair. If flow can be in both directions, two transformation matrices are needed.

Let $m_b$ be a vector, each of the entries of which is an amount of the corresponding base component; $m_i$ be a vector, each of the entries of which is an amount of the corresponding pseudocomponent in pseudocomponent set i; and $P_i$ be a matrix, each column of which defines a pseudocomponent in pseudocomponent set i. Then $$m_b = P_i m_i \qquad (11)$$

$m_i$ contains fewer entries than $m_b$, and correspondingly $P_i$ contains fewer columns than rows.

Given a second set of pseudocomponents, indicated by the subscript j, $$m_b = P_j m_j \qquad (12)$$

It is desired to determine the $m_j$ that yields a base composition as nearly as possible the same as that corresponding to $m_i$. In other words, as nearly as possible, it is desired that $$P_j m_j = P_i m_i \qquad (13)$$

Projection from the space of $P_i$ to the space of $P_j$ is performed by premultiplying Eq. (13) by the transpose of $P_j$. The solution of the resulting set of equations is $$m_j = (P_j^T P_j)^{-1} P_j^T P_i m_i \qquad (14)$$

If there are more pseudocomponents in set j than in set i, the equality can be satisfied exactly. If there are more in set i, then it can be satisfied only approximately.

It is also necessary to determine the pseudocomponent characterization for each computational region. This includes parameters used in computing density, viscosity, and phase equilibrium. They are computed so that the fluid properties, such as viscosity or density, of a pseudocomponent mixture are the same, or as nearly as possible the same, as of the mixture of base components having the same composition as the pseudocomponent mixture. This computation is needed regardless of the type of pseudocomponents (such as lumped pseudocomponents) being used, and those skilled in the art of computations using pseudocomponents will be familiar with how it can be done. As an example, consider the computation of fugacity coefficients using a general form of the cubic equation of state, as described in a paper by K. H. Coats, "Simulation of Gas Condensate Reservoir Performance," SPE 10512 presented at the Sixth SPE Symposium on Reservoir Simulation, New Orleans, La., Jan. 31–Feb. 3, 1982. In matrix-vector form, the computations proceed as follows. Let the elements of the matrix A be $$A_{kl} = (1 - \delta_{kl})(\alpha_k \alpha_l)^{1/2} \qquad (15)$$

where the $\delta_{kl}$ are the binary interaction parameters, and $$\alpha_k = \frac{a_k p_{rk}}{T_{rk}^2} \qquad (16)$$

where the subscript k indicates the base component, $\alpha_k$ is a parameter for component k that depends on the particular cubic equation of state being used, $p_{rk}$ is the reduced pressure of component k, and $T_{rk}$ is the reduced temperature of component k. $\alpha_l$ is similarly defined. Let the elements of the vector B be $$B_k = \frac{b_k p_{rk}}{T_{rk}} \qquad (17)$$

where $b_k$ is a parameter for component k that depends on the particular cubic equation of state being used.

Given A, B, and $x_b$, the base composition of the fluid being represented, the following two scalars are computed.

$$a = x_b^T A x_b \qquad (18)$$

$$b = x_b^T B \qquad (19)$$

Given these scalars, the following cubic equation is solved for Z, the compressibility factor.

$$Z^3 + [(m_1 + m_2 - 1)b - 1]Z^2 + [a + m_1 m_2 b^2 - (m_1 + m_2)b(b + 1)]Z - \qquad (20)$$
$$[ab + m_1 m_2 b^2 (b + 1)] = 0$$

Given Z, the logarithm of the fugacity coefficient vector is computed by $$\ln \psi = -[\ln(Z - b)]e + \qquad (21)$$
$$\left[ \frac{a}{(m_1 - m_2)b} \ln\left( \frac{Z + m_2 b}{Z + m_1 b} \right) \right] \left[ \frac{2}{a} A x_b - \frac{1}{b} B \right] + \left( \frac{Z - 1}{b} \right) B$$

In this sequence of computations, the only place composition appears is Eqs. (18), (19), and (21). In one embodiment of this invention, Eqs. (18) and (19) are replaced by $$a = x_i^T A_{ii} x_i \qquad (22)$$

$$b = x_i^T B_i \qquad (23)$$

where $$A_{ii} = P_i^T A P_i \qquad (24)$$

$$B_i = P_i^T B \qquad (25)$$

In Eq. (21), $Ax_b$ is replaced by $A_i x_i$, where $$A_i = A P_i \qquad (26)$$

Given these effective properties, compositional computations using pseudocomponents are performed in substantially the same way that conventional compositional computations are performed, which is known to those skilled in the art.

At this point, it is desirable to verify the pseudocomponent definitions by rerunning the simplified models. Comparing the results to those obtained using the base components makes it possible to decide whether the chosen pseudocomponent representation is adequate.

Next, the actual detailed simulations are performed using the pseudocomponents. As noted above, the computations are substantially unaffected by the fact that the components being used are actually pseudocomponents.

The results obtained using pseudocomponents can be transformed in the practice of this invention back to representations in terms of the base components. This corresponds to the delumping procedure sometimes used in connection with lumped pseudocomponent calculations. A process for transforming pseudocomponent compositions back to base compositions is provided in more detail in the following example.

EXAMPLE

This example is provided to further illustrate the practice of this invention. This example illustrates construction of a set of pseudocomponents, computation of a pseudocomponent composition corresponding to a given base composition, computation of a base composition corresponding to a given pseudocomponent composition, and transformation from one pseudocomponent composition to another.

The data provided in this example was based on a real reservoir fluid. Using available data from laboratory tests performed on reservoir samples of the reservoir fluid, a base characterization of the fluid using 13 components was developed. Seven of the components corresponded to either pure compounds (C1, CO2, and C2) or single carbon numbers including isomers thereof (C3, C4, C5, and C6). The remaining six components corresponded to ranges of carbon numbers. These components were designated C7.1, C7.2, C7.3, C7.4, C7.5, and C7.6. The characterization used the Peng-Robinson equation of state parameters tuned to match as well as possible laboratory measurements. Those skilled in the art are familiar with such fluid characterizations.

The base characterization was then used to perform a series of six vapor-liquid equilibrium calculations on each of two fluid samples: one that was liquid at reservoir conditions and one that was vapor at the same conditions. Each equilibrium calculation resulted in two compositions, therefore the 12 equilibrium calculations yielded 24 compositions, the results of which are illustrated in Table E1 below. Each row of Table E1 represents one of the 24 compositions.

For the purposes of this example, Table E1 was assumed to contain the base compositions predicted to occur in the computations of interest. For a full-scale simulation, it would be preferable to generate the predicted base compositions by performing a simplified version of the simulation of interest. However, this set of 24 base compositions suffices to illustrate the process of the invention while being small enough to be presented conveniently.

A singular value decomposition of the matrix in Table E1 was performed. Singular value decomposition produces three results: the singular values, the left singular vectors, and the right singular vectors. Only the singular values and right singular vectors are needed. These are presented in Tables E2 and E3, respectively. The singular values provide guidance regarding the number of pseudocomponents to use, and the right singular vectors are used to generate the pseudocomponents.

The fact that the fifth singular value is only slightly smaller than the fourth, while the fourth is significantly smaller than the third, and the sixth significantly smaller than the fifth, suggest using either three or five pseudocomponents. For simplicity of presentation, the construction of three pseudocomponents is described; however, additional pseudocomponents could have been constructed. The three pseudocomponents are generated from the first three right singular vectors. The first three rows of Table E3 contain the transposes of these and the results are graphically displayed in FIG. 2. The first step is to select the dominant component of the first right singular vector. This is the component with the largest entry; this component is C1. Using a process similar to Gaussian elimination, the entry for this component is eliminated from the other two right singular vectors. Referring to Table E3, the first row is multiplied by the quantity obtained by dividing the C1 entry in the second row by the C1 entry in the first row. This quantity is −1357/0.9770, or −0.1361. The first row is multiplied by this quantity, and the result is subtracted from the second. The result is a C1 entry equal to zero in the second row. A similar process is used to obtain a zero C1 entry in the third row. The result is shown in Table E4 and graphically illustrated in FIG. 3. The vectors are no longer right singular vectors, but they are not yet pseudocomponent definitions, so they are referred to as intermediate vectors.

The next step is to select the dominant component for the second vector; this dominant component is C7.2. The entry for this component is eliminated from the first and third vectors using the procedure described in the preceding paragraph. The result is shown in Table E5 and FIG. 4. Following this, the procedure is repeated for the third vector, the dominant component of which is C7.3. The result is shown in Table E6 and graphically illustrated in FIG. 5.

Finally, the actual pseudocomponents are generated by normalizing the intermediate vectors shown in Table E6 such that their entries sum to one. The result is shown in Table E7 and graphically illustrated in FIG. 6 where lines 1, 2, and 3 represent pseudocomponents 1, 2, and 3, respectively.

For purposes of comparison, the least squares pseudocomponents corresponding to the same set of dominant components are presented in Table E8. They are generally similar to the pseudocomponents shown in Table E7.

If it is desired to transform a fluid from one pseudocomponent representation to another, this can be done by first transforming (delumping) the first pseudocomponent representation to a base component representation and then transforming the base component representation to the second pseudocomponent representation. Consider the transformation of pseudocomponent compositions. Given a composition expressed as $i$ pseudocomponent mole fractions, the corresponding base composition is $$x_b = P_i x_i \quad \text{(E1)}$$

The pseudocomponent composition that most closely corresponds to a given base composition in a least squares sense is given by $$x_i = (P_i^T P_i)^{-1} P_i^T x_b \quad \text{(E2)}$$

For the three pseudocomponents given by Table E7, $(P_i^T P_i)^{-1} P_i^T$ is given by Table E9.

Of the 24 base compositions in Table E1, the one composition least well represented by three pseudocomponents is the $19^{th}$. The three-pseudocomponent composition corresponding to it is $$x_3 = \begin{bmatrix} 0.5415 \\ 0.1117 \\ 0.3667 \end{bmatrix} = (P_3^T P_3)^{-1} P_3^T \begin{bmatrix} 0.4230 \\ 0.0872 \\ 0.0507 \\ 0.0320 \\ 0.0244 \\ 0.0229 \\ 0.0194 \\ 0.0907 \\ 0.0937 \\ 0.1015 \\ 0.0420 \\ 0.0118 \\ 0.0009 \end{bmatrix} \quad \text{(E3)}$$

As shown above, the 13 base-component mole fractions appear not to sum to one, but this is because the mole fractions have been rounded to four decimal places for presentation. The three pseudocomponent mole fractions computed above, on the other hand, in actuality do not sum to one, because the computation used to determine them does not ensure that they do so. If desired, they can be normalized.

The corresponding base composition is computed using Eq. (E1).

$$x_{b,3} = P_3 \begin{bmatrix} 0.5415 \\ 0.1117 \\ 0.3667 \end{bmatrix} = \begin{bmatrix} 0.4226 \\ 0.0894 \\ 0.0505 \\ 0.0332 \\ 0.0261 \\ 0.0224 \\ 0.2080 \\ 0.0997 \\ 0.0968 \\ 0.0773 \\ 0.0337 \\ 0.0229 \\ 0.0246 \end{bmatrix} \quad \text{(E4)}$$

Figure 7:
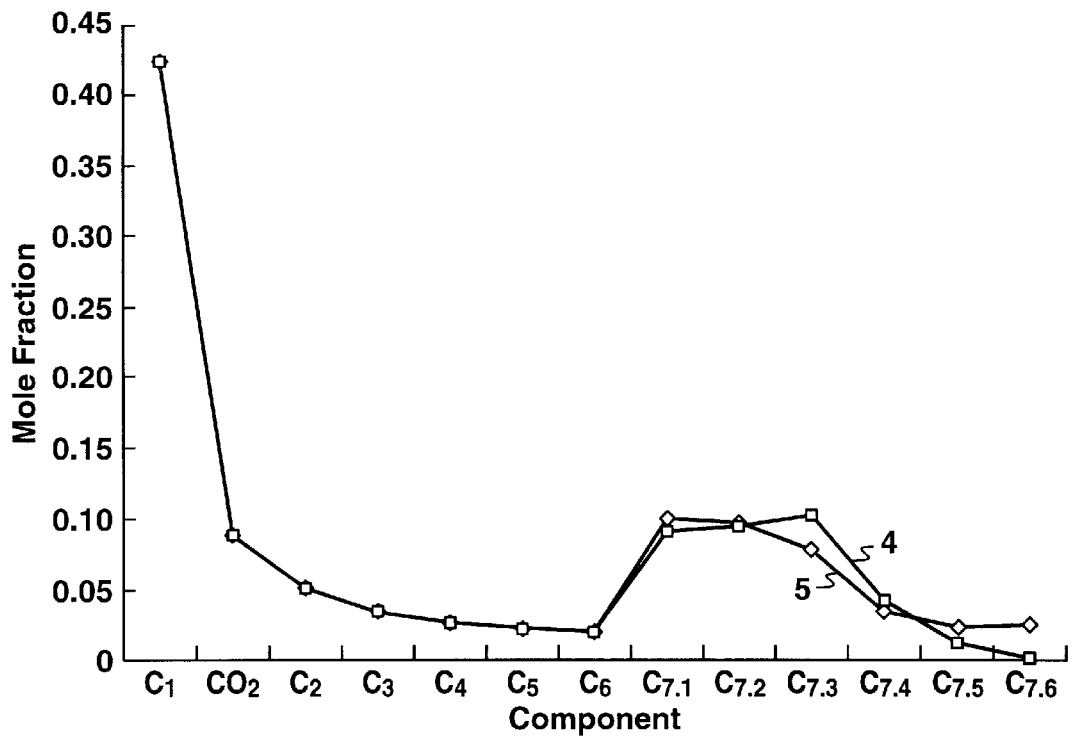
FIG. 7 illustrates in graphical form a comparison of an origin base composition with a computed base composition derived from a five-pseudocomponent representation.

The two composition vectors are plotted in FIG. 7 where line 4 represents the mole fractions of the 13 base components and line 5 represents the mole fractions estimated using three pseudocomponents. The agreement between them, though not perfect, is quite good given that only three pseudocomponents are being used and this is the composition that is reproduced least well by the three pseudocomponents.

Table E10 contains the pseudocomponent definitions for five pseudocomponents. The five-pseudocomponent composition of the $19^{th}$ observation is $$x_5 = \begin{bmatrix} 0.4495 \\ 0.2250 \\ 0.1993 \\ 0.1285 \\ -0.0007 \end{bmatrix} = (P_5^T P_5)^{-1} P_5^T \begin{bmatrix} 0.4230 \\ 0.0872 \\ 0.0507 \\ 0.0320 \\ 0.0244 \\ 0.0229 \\ 0.0194 \\ 0.0907 \\ 0.0937 \\ 0.1015 \\ 0.0420 \\ 0.0118 \\ 0.0009 \end{bmatrix} \quad \text{(E5)}$$

The corresponding base composition, computed using Eq. (E1), is $$x_{b,5} = \begin{bmatrix} 0.4495 \\ 0.2250 \\ 0.1993 \\ 0.1285 \\ -0.0007 \end{bmatrix} = \begin{bmatrix} 0.4230 \\ 0.0868 \\ 0.0512 \\ 0.0325 \\ 0.0249 \\ 0.0234 \\ 0.0194 \\ 0.0897 \\ 0.0947 \\ 0.1012 \\ 0.0407 \\ 0.0145 \\ -0.0003 \end{bmatrix} \quad (E6)$$

Figure 8:
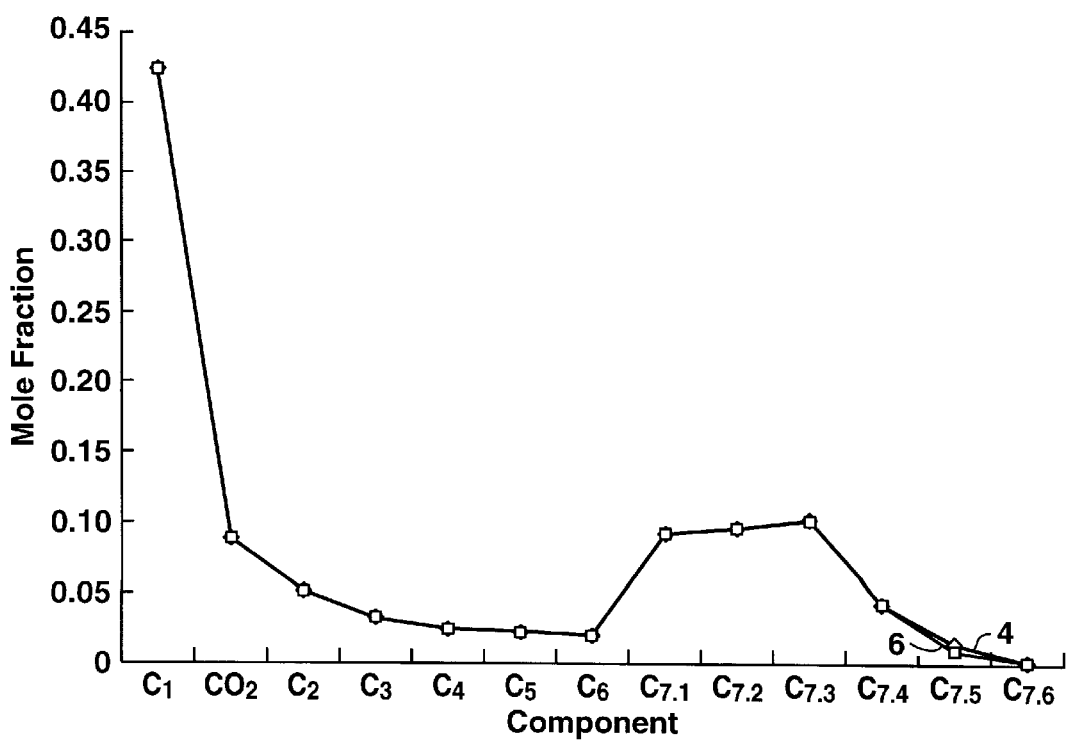
FIG. 8 illustrates in graphical form a comparison of an origin base composition with a computed base composition derived from a three-pseudocomponent composition.

FIG. 8 compares this approximate composition with the original where line 4 represents the mole fractions of the base components and line 6 represents the mole fractions using five pseudocomponents. The agreement is very good—lines 4 and 6 are virtually superposed for all 13 base components.

If there are two computational regions, one using three pseudocomponents and one using five, any fluid moving between the two must be transformed from one representation to the other. For flow from the five-pseudocomponent region to the three pseudocomponent region, the necessary transformation is $$x_3 = (P_3^T P_3)^{-1} P_3^T P_5 x_5 \quad (E7)$$

Table E12 contains the transformation matrix, $(P_3^T P_3)^{-1} P_3^T P_5$. The three-pseudocomponent composition resulting from transforming the five-pseudocomponent composition in Eq. (E6) is $$x_3 = \begin{bmatrix} 0.5415 \\ 0.1117 \\ 0.3667 \end{bmatrix} \quad (E8)$$

This composition is identical to that obtained by transforming the original base composition to three pseudocomponents, as can be seen by comparing Eqs. (E8) and (E3).

If flow is from the three-pseudocomponent region to the five-pseudocomponent region, the transformation used is $$x_5 = (P_5^T P_5)^{-1} P_5^T P_3 x_3 \quad (E9)$$

Table E13 contains the transformation matrix, $(P_5^T P_5)^{-1} P_5^T P_3$. The result of transforming the three-pseudocomponent composition given in Eq. (E8) is $$x_5 = \begin{bmatrix} 0.4491 \\ 0.2300 \\ 0.1522 \\ 0.1324 \\ 0.0562 \end{bmatrix} \quad (E10)$$

This composition differs somewhat from the starting composition of Eq. (E6). The underlying base composition is unchanged from that corresponding to three pseudocomponents, as given in Eq. (E4).

Persons skilled in the art will readily understand that the present invention is computationally intense. Accordingly, use of a computer, preferably a digital computer, to practice the invention is virtually a necessity. A large number of iterative calculations and large computer storage space is typically required. Computer software for various portions of the method is commercially available, for example, to develop gridcells, display results, and to calculate fluid properties from an equation of state.

The invention is not to be unduly limited to the foregoing which has been set forth for illustrative purposes. On the contrary, a wide variety of modifications and alternative embodiments will be apparent to persons skilled in the art without departing from the true scope of the invention as defined in the claims set forth below.

TABLE E1

Set of Base Compositions Predicted to Occur in Process of Interest

Table E1 contains 24 rows and 13 columns. Each column corresponds to a component. The components are ordered left to right from most volatile to least volatile. Each row defines a base composition in terms of mole fractions. Since mole fractions must sum to the elements in each row add up to one within the accuracy possible given the number of digits printed. The compositions of the first and second rows, and of each subsequent pairs of rows, are in equilibrium with each other at a certain pressure and temperature. The first six pairs of rows correspond to a fluid that is liquid at reservoir conditions, and the remaining six pairs to a fluid that is vapor at reservoir conditions.

|    | C1      | C02     | C2      | C3      | C4      | C5      | C6      | C7.1    | C7.2    | C7.3    | C7.4    | C7.5    | C7.6    |
|----|---------|---------|---------|---------|---------|---------|---------|---------|---------|---------|---------|---------|---------|
| 1  | 0.14235 | 0.05893 | 0.04326 | 0.03982 | 0.03756 | 0.02879 | 0.02802 | 0.13602 | 0.13154 | 0.13970 | 0.07366 | 0.06311 | 0.07724 |
| 2  | 0.73318 | 0.14526 | 0.06605 | 0.02953 | 0.01272 | 0.00490 | 0.00246 | 0.00498 | 0.00086 | 0.00005 | 0.00000 | 0.00000 | 0.00000 |
| 3  | 0.25952 | 0.08496 | 0.05289 | 0.03994 | 0.03285 | 0.02354 | 0.02219 | 0.10625 | 0.10224 | 0.10882 | 0.05740 | 0.04919 | 0.06021 |
| 4  | 0.75702 | 0.13261 | 0.05770 | 0.02521 | 0.01134 | 0.00486 | 0.00281 | 0.00653 | 0.00171 | 0.00019 | 0.00002 | 0.00000 | 0.00000 |
| 5  | 0.34974 | 0.09604 | 0.05469 | 0.03736 | 0.02871 | 0.01988 | 0.01839 | 0.08709 | 0.08328 | 0.08872 | 0.04683 | 0.04014 | 0.04913 |
| 6  | 0.76183 | 0.12390 | 0.05426 | 0.02471 | 0.01202 | 0.00571 | 0.00370 | 0.00962 | 0.00349 | 0.00065 | 0.00010 | 0.00001 | 0.00000 |
| 7  | 0.38666 | 0.09900 | 0.05478 | 0.03620 | 0.02714 | 0.01854 | 0.01700 | 0.07910 | 0.07598 | 0.08081 | 0.04265 | 0.03656 | 0.04476 |
| 8  | 0.76046 | 0.12076 | 0.05340 | 0.02491 | 0.0#256 | 0.00622 | 0.00422 | 0.01144 | 0.00472 | 0.00109 | 0.00019 | 0.00002 | 0.00000 |
| 9  | 0.41921 | 0.10103 | 0.05469 | 0.03521 | 0.02585 | 0.01744 | 0.01587 | 0.07388 | 0.06973 | 0.07387 | 0.03896 | 0.03339 | 0.04088 |
| 10 | 0.75754 | 0.11819 | 0.05285 | 0.02524 | 0.01313 | 0.00674 | 0.00474 | 0.01333 | 0.00613 | 0.00170 | 0.00035 | 0.00005 | 0.00000 |
| 11 | 0.43640 | 0.10190 | 0.05460 | 0.03470 | 0.02520 | 0.01690 | 0.01530 | 0.07080 | 0.06650 | 0.07020 | 0.03700 | 0.03170 | 0.03880 |
| 12 | 0.75532 | 0.11692 | 0.05262 | 0.02546 | 0.01346 | 0.00704 | 0.00505 | 0.01444 | 0.00700 | 0.00214 | 0.00047 | 0.00008 | 0.00000 |
| 13 | 0.16858 | 0.04405 | 0.03324 | 0.03026 | 0.03311 | 0.04256 | 0.04689 | 0.24634 | 0.23963 | 0.09167 | 0.02015 | 0.00331 | 0.00021 |

TABLE E1-continued

Set of Base Compositions Predicted to Occur in Process of Interest

Table E1 contains 24 rows and 13 columns. Each column corresponds to a component. The components are ordered left to right from most volatile to least volatile. Each row defines a base composition in terms of mole fractions. Since mole fractions must sum to the elements in each row add up to one within the accuracy possible given the number of digits printed. The compositions of the first and second rows, and of each subsequent pairs of rows, are in equilibrium with each other at a certain pressure and temperature. The first six pairs of rows correspond to a fluid that is liquid at reservoir conditions, and the remaining six pairs to a fluid that is vapor at reservoir conditions.

|    | C1      | C02     | C2      | C3      | C4      | C5      | C6      | C7.1    | C7.2    | C7.3    | C7.4    | C7.5    | C7.6    |
|----|---------|---------|---------|---------|---------|---------|---------|---------|---------|---------|---------|---------|---------|
| 14 | 0.78962 | 0.10617 | 0.04956 | 0.02192 | 0.01101 | 0.00712 | 0.00405 | 0.00896 | 0.00156 | 0.00003 | 0.00000 | 0.00000 | 0.00000 |
| 15 | 0.30365 | 0.07003 | 0.04636 | 0.03505 | 0.03182 | 0.03478 | 0.03355 | 0.16512 | 0.17033 | 0.08583 | 0.01994 | 0.00332 | 0.00022 |
| 16 | 0.78651 | 0.10558 | 0.04926 | 0.02181 | 0.01104 | 0.00730 | 0.00436 | 0.01081 | 0.00315 | 0.00018 | 0.00001 | 0.00000 | 0.00000 |
| 17 | 0.39318 | 0.08325 | 0.05010 | 0.03319 | 0.02654 | 0.02595 | 0.02282 | 0.10879 | 0.11638 | 0.10183 | 0.03143 | 0.00614 | 0.00041 |
| 18 | 0.78038 | 0.10505 | 0.04919 | 0.02197 | 0.01132 | 0.00769 | 0.00479 | 0.01309 | 0.00554 | 0.00089 | 0.00008 | 0.00000 | 0.00000 |
| 19 | 0.42298 | 0.08715 | 0.05069 | 0.03200 | 0.02443 | 0.02289 | 0.01937 | 0.09071 | 0.09372 | 0.10147 | 0.04195 | 0.01176 | 0.00088 |
| 20 | 0.77779 | 0.10490 | 0.04919 | 0.02205 | 0.01143 | 0.00782 | 0.00492 | 0.01379 | 0.00635 | 0.00152 | 0.00022 | 0.00001 | 0.00000 |
| 21 | 0.44059 | 0.08997 | 0.05101 | 0.03100 | 0.02282 | 0.02065 | 0.01692 | 0.07843 | 0.07699 | 0.08859 | 0.04657 | 0.03051 | 0.00595 |
| 22 | 0.77614 | 0.10481 | 0.04920 | 0.02209 | 0.01149 | 0.00789 | 0.00499 | 0.01415 | 0.00677 | 0.00200 | 0.00041 | 0.00005 | 0.00000 |
| 23 | 0.44739 | 0.09195 | 0.05133 | 0.03033 | 0.02174 | 0.01920 | 0.01537 | 0.07162 | 0.06716 | 0.07078 | 0.03748 | 0.03172 | 0.04394 |
| 24 | 0.77590 | 0.10480 | 0.04920 | 0.02210 | 0.01150 | 0.00790 | 0.00500 | 0.01420 | 0.00682 | 0.00206 | 0.00045 | 0.00007 | 0.00000 |

TABLE E2

Singular Values and Related Information

Table E2 contains the singular values resulting from performing a singular value decomposition on the matrix in Table 1. The singular values are ordered top to bottom from largest to smallest. The cumulative sum of squares is accumulated from the bottom. It is the error, expressed as a sum of squares, that would result if the original matrix were approximated by the singular vectors, omitting the one corresponding to the current row and the rows below it. For example, if the first three singular vectors were used, the sum of the squares of the error would be that corresponding to the fourth singular value; this error is 7.91E − 03. If the first four singular vectors were used, the error would drop to 3.85E − 03, and if the first five were used, it would drop to 4.03E − 04. This indicates that more accuracy improvement will result by going from four singular vectors to five than by going from three singular vectors to four.

| Singular Value Number | Singular Value | Singular Value Squared | Cumulative Sum of Squares | Square Root of Cumulative |
|---|---|---|---|---|
| 1 | 3.01E + 00 | 9.06E + 00 | 9.53E + 00 | 3.09E + 00 |
| 2 | 6.50E − 01 | 4.23E − 01 | 4.66E − 01 | 6.82E − 01 |
| 3 | 1.88E − 01 | 3.53E − 02 | 4.32E − 02 | 2.08E − 01 |
| 4 | 6.31E − 02 | 4.06E − 03 | 7.91E − 03 | 8.89E − 02 |
| 5 | 5.87E − 02 | 3.45E − 03 | 3.85E − 03 | 6.20E − 02 |
| 6 | 1.72E − 02 | 2.96E − 04 | 4.03E − 04 | 2.01E − 02 |
| 7 | 7.79E − 03 | 6.07E − 05 | 1.07E − 04 | 1.03E − 02 |
| 8 | 5.37E − 03 | 2.88E − 05 | 4.60E − 05 | 6.79E − 03 |
| 9 | 3.55E − 03 | 1.26E − 05 | 1.72E − 05 | 4.1SE − 03 |
| 10 | 1.93E − 03 | 3.72E − 06 | 4.61E − 06 | 2.15E − 03 |
| 11 | 9.39E − 04 | 8.82E − 07 | 8.84E − 07 | 9.40E − 04 |
| 12 | 4.32E − 05 | 1.87E − 09 | 1.87E − 09 | 4.32E − 05 |
| 13 | 2.02E − 06 | 4.08E − 12 | 4.07E − 12 | 2.02E − 06 |

TABLE E3

Right Singular Vectors

Table E3 contains the right singular vectors resulting from applying singular value decomposition to the matrix in Table E1. Each the following table contains one right singular vector. The first is the most significant (i.e., has the largest singular value), and each successive right singular vector is less significant. The sum of the squares of the entries in each row is one. The rows are mutually orthogonal. As a result, the matrix made up of the right singular vectors is orthonormal.

|    | C1      | C02     | C2      | C3      | C4      | C5      | C6      | C7.1    | C7.2    | C7.3    | C7.4    | C7.5    | C7.6    |
|----|---------|---------|---------|---------|---------|---------|---------|---------|---------|---------|---------|---------|---------|
| 1  | 0.9770  | 0.1628  | 0.0797  | 0.0417  | 0.0258  | 0.0184  | 0.0148  | 0.0617  | 0.0540  | 0.0455  | 0.0204  | 0.0138  | 0.0143  |
| 2  | −0.1357 | 0.1197  | 0.1107  | 0.1104  | 0.1117  | 0.1104  | 0.1114  | 0.5679  | 0.5725  | 0.4352  | 0.1837  | 0.1224  | 0.1314  |
| 3  | −0.0558 | 0.2601  | 0.1485  | 0.1078  | 0.0627  | −0.0381 | −0.0588 | −0.3475 | −0.3571 | 0.3779  | 0.3538  | 0.3798  | 0.4757  |
| 4  | 0.0011  | 0.0040  | −0.0447 | 0.0083  | 0.0310  | −0.0249 | 0.0397  | 0.2669  | 0.0526  | −0.6181 | −0.1721 | 0.2371  | 0.6730  |
| 5  | −0.1532 | 0.8432  | 0.3199  | 0.1370  | 0.0233  | −0.0447 | −0.0345 | −0.0220 | 0.0425  | −0.2203 | −0.1843 | −0.1679 | −0.1665 |
| 6  | −0.0075 | 0.1075  | −0.0737 | −0.1286 | −0.1237 | −0.0538 | 0.0079  | 0.2516  | −0.1305 | −0.3041 | 0.4329  | 0.6045  | −0.4718 |
| 7  | −0.0028 | −0.2616 | 0.2987  | 0.4946  | 0.4755  | 0.2061  | 0.0845  | −0.2710 | 0.1588  | −0.1380 | −0.1895 | 0.3533  | −0.2086 |
| 8  | −0.0019 | −0.1189 | 0.5387  | −0.3470 | −0.5171 | 0.4147  | −0.0704 | −0.2180 | 0.2456  | −0.0481 | −0.0338 | 0.1299  | 0.0527  |
| 9  | −0.0120 | −0.2232 | 0.5048  | 0.2217  | 0.0447  | 0.0658  | 0.0666  | 0.3211  | −0.3726 | −0.1727 | 0.4293  | −0.4224 | 0.0304  |
| 10 | −0.0019 | 0.1536  | −0.3775 | −0.0048 | 0.1615  | 0.5380  | 0.1175  | −0.2910 | 0.2384  | −0.2441 | 0.4889  | −0.2456 | 0.0638  |
| 11 | −0.0132 | 0.1061  | −0.1994 | 0.1668  | −0.1635 | 0.6411  | 0.1770  | 0.2837  | −0.4592 | 0.1719  | −0.3456 | 0.1007  | −0.0377 |

TABLE E3-continued

Right Singular Vectors

Table E3 contains the right singular vectors resulting from applying singular value decomposition to the matrix in Table E1. Each the following table contains one right singular vector. The first is the most significant (i.e., has the largest singular value), and each successive right singular vector is less significant. The sum of the squares of the entries in each row is one. The rows are mutually orthogonal. As a result, the matrix made up of the right singular vectors is orthonormal.

|    | C1      | CO2     | C2      | C3      | C4      | C5      | C6     | C7.1    | C7.2    | C7.3    | C7.4    | C7.5    | C7.6    |
|----|---------|---------|---------|---------|---------|---------|--------|---------|---------|---------|---------|---------|---------|
| 12 | −0.0071 | 0.0327  | 0.1584  | −0.5300 | 0.3413  | −0.0496 | 0.7439 | −0.0397 | −0.1088 | 0.0405  | −0.0717 | 0.0157  | −0.0070 |
| 13 | 0.0045  | −0.0254 | −0.0900 | 0.4649  | −0.5489 | −0.2424 | 0.6056 | −0.1623 | 0.1275  | −0.0279 | 0.0686  | −0.0043 | 0.0168  |

TABLE E4

Intermediate Vectors Following Step 1

The first row still contains the first right singular vector. The largest entry in it is the one for C1. As a result, C1 is the dominant component. The second and third rows are modified by adding to them the first row multiplied by a quantity such that the entry for C1 becomes zero, as shown.

|   | C1     | CO2    | C2     | C3     | C4     | C5      | C6      | C7.1    | C7.2    | C7.3   | C7.4   | C7.5   | C7.6   |
|---|--------|--------|--------|--------|--------|---------|---------|---------|---------|--------|--------|--------|--------|
| 1 | 0.9770 | 0.1628 | 0.0797 | 0.0417 | 0.0258 | 0.0184  | 0.0148  | 0.0617  | 0.0540  | 0.0455 | 0.0204 | 0.0138 | 0.0143 |
| 2 | 0      | 0.1423 | 0.1218 | 0.1162 | 0.1153 | 0.1129  | 0.1134  | 0.5765  | 0.5800  | 0.4415 | 0.1866 | 0.1244 | 0.1334 |
| 3 | 0      | 0.2694 | 0.1531 | 0.1102 | 0.0642 | −0.0370 | −0.0580 | −0.3439 | −0.3540 | 0.3805 | 0.3550 | 0.3806 | 0.4765 |

TABLE E5

Intermediate Vectors Following Step 2

The second row still contains the intermediate vector from the first step. The largest entry in it is the one for C7.2. The first and third rows of Table E4 are modified by adding to them the second row times a quantity such that the entry for C7.2 becomes zero, as shown.

|   | C1     | CO2    | C2     | C3     | C4     | C5     | C6     | C7.1   | C7.2   | C7.3   | C7.4   | C7.5   | C7.6   |
|---|--------|--------|--------|--------|--------|--------|--------|--------|--------|--------|--------|--------|--------|
| 1 | 0.9770 | 0.1496 | 0.0684 | 0.0309 | 0.0151 | 0.0079 | 0.0043 | 0.0081 | 0      | 0.0044 | 0.0030 | 0.0023 | 0.0019 |
| 2 | 0.0000 | 0.1423 | 0.1218 | 0.1162 | 0.1153 | 0.1129 | 0.1134 | 0.5765 | 0.5800 | 0.4415 | 0.1866 | 0.1244 | 0.1334 |
| 3 | 0.0000 | 0.3563 | 0.2274 | 0.1811 | 0.1346 | 0.0319 | 0.0112 | 0.0079 | 0      | 0.6499 | 0.4688 | 0.4565 | 0.5579 |

TABLE E6

Intermediate Vectors Following Step 3

The third row still contains the intemiediate vector from the second step. The largest entry in it is the one for C7.3. The first and second rows of Table E5 are modified by adding to them the third row times a quantity such that the entry for C7.3 becomes zero, as shown.

|   | C1     | CO2     | C2      | C3      | C4     | C5     | C6     | C7.1   | C7.2   | C7.3   | C7.4    | C7.5    | C7.6    |
|---|--------|---------|---------|---------|--------|--------|--------|--------|--------|--------|---------|---------|---------|
| 1 | 0.9770 | 0.1472  | 0.0668  | 0.0297  | 0.0142 | 0.0077 | 0.0042 | 0.0080 | 0.0000 | 0.0000 | −0.0001 | −0.0008 | −0.0019 |
| 2 | 0.0000 | −0.0997 | −0.0327 | −0.0068 | 0.0239 | 0.0913 | 0.1058 | 0.5711 | 0.5800 | 0.0000 | −0.1319 | −0.1857 | −0.2456 |
| 3 | 0.0000 | 0.3563  | 0.2274  | 0.1811  | 0.1346 | 0.0319 | 0.0112 | 0.0079 | 0.0000 | 0.6499 | 0.4688  | 0.4565  | 0.5579  |

TABLE E7

Three-Pseudocomponent Definition Vectors

The intermediate vectors following step 3 are normalized such that their entries sum to one. The result is the pseudocomponent definitions in terms of their base compositions.

|   | C1     | CO2     | C2      | C3      | C4     | C5     | C6     | C7.1   | C7.2   | C7.3   | C7.4    | C7.5    | C7.6    |
|---|--------|---------|---------|---------|--------|--------|--------|--------|--------|--------|---------|---------|---------|
| 1 | 0.7804 | 0.1176  | 0.0534  | 0.0237  | 0.0113 | 0.0062 | 0.0034 | 0.0064 | 0.0000 | 0.0000 | −0.0001 | −0.0007 | −0.0015 |
| 2 | 0.0000 | −0.1489 | −0.0488 | −0.0102 | 0.0357 | 0.1363 | 0.1580 | 0.8529 | 0.8661 | 0.0000 | −0.1970 | −0.2773 | −0.3667 |
| 3 | 0.0000 | 0.1155  | 0.0737  | 0.0587  | 0.0436 | 0.0103 | 0.0036 | 0.0026 | 0.0000 | 0.2108 | 0.1521  | 0.1480  | 0.1809  |

TABLE E8

Three-Pseudocomponent Definition Vectors Obtained by Least Squares
Using the three dominant components of the pseudocomponents in Table E7, the following
pseudocomponents are determined by squares followed by normalization of the resulting vectors.

|   | C1 | CO2 | C2 | C3 | C4 | C5 | C6 | C7.1 | C7.2 | C7.3 | C7.4 | C7.5 | C7.6 |
|---|---|---|---|---|---|---|---|---|---|---|---|---|---|
| 1 | 0.7779 | 0.1177 | 0.0534 | 0.0238 | 0.0114 | 0.0061 | 0.0034 | 0.0066 | 0.0000 | 0.0000 | 0.0002 | −0.0001 | −0.0005 |
| 2 | 0.0000 | −0.0582 | −0.0126 | 0.0106 | 0.0387 | 0.0972 | 0.1163 | 0.6292 | 0.6242 | 0.0000 | −0.1209 | −0.1489 | −0.1755 |
| 3 | 0.0000 | 0.1065 | 0.0728 | 0.0579 | 0.0432 | 0.0125 | 0.0029 | −0.0051 | 0.0000 | 0.2428 | 0.1636 | 0.1427 | 0.1601 |

TABLE E9

Base Representation to Three Pseudocomponent Representation Transformation Matrix
Multiplying the matrix in Table E9 by a base composition vector (comprising 13 base
component mole fractions) yields the pseudocomponent composition (comprising three pseudocomponent
mole fractions) that best approximates the original base composition.

|   | C1 | CO2 | C2 | C3 | C4 | C5 | C6 | C7.1 | C7.2 | C7.3 | C7.4 | C7.5 | C7.6 |
|---|---|---|---|---|---|---|---|---|---|---|---|---|---|
| 1 | 1.2507 | 0.1645 | 0.0699 | 0.0254 | 0.0084 | 0.0066 | 0.0034 | 0.0033 | −0.0064 | −0.0457 | −0.0317 | −0.0311 | −0.0389 |
| 2 | −0.0058 | −0.0180 | 0.0170 | 0.0311 | 0.0496 | 0.0898 | 0.0988 | 0.5225 | 0.5290 | 0.1347 | −0.0231 | −0.0748 | −0.1083 |
| 3 | −0.1692 | 0.7486 | 0.5121 | 0.4302 | 0.3487 | 0.1636 | 0.1277 | 0.5630 | 0.5536 | 1.5858 | 1.0181 | 0.9366 | 1.1272 |

TABLE E10

Five-Pseudocomponent Definition Vectors

|   | C1 | CO2 | C2 | C3 | C4 | C5 | C6 | C7.1 | C7.2 | C7.3 | C7.4 | C7.5 | C7.6 |
|---|---|---|---|---|---|---|---|---|---|---|---|---|---|
| 1 | 0.9410 | 0.0000 | 0.0061 | 0.0003 | 0.0046 | 0.0131 | 0.0080 | 0.0196 | 0.0000 | 0.0000 | 0.0039 | 0.0034 | 0.0000 |
| 2 | 0.0000 | 0.0000 | 0.0104 | 0.0256 | 0.0415 | 0.0649 | 0.0821 | 0.4448 | 0.4206 | 0.0000 | −0.0547 | −0.0352 | 0.0000 |
| 3 | 0.0000 | 0.0000 | 0.0526 | 0.0463 | 0.0394 | 0.0321 | −0.0016 | −0.0605 | 0.0000 | 0.5078 | 0.2686 | 0.1154 | 0.0000 |
| 4 | 0.0000 | 0.6752 | 0.2776 | 0.1357 | 0.0441 | −0.0270 | −0.0183 | −0.0548 | 0.0000 | 0.0000 | −0.0172 | −0.0153 | 0.0000 |
| 5 | 0.0000 | 0.0000 | 0.0107 | 0.0394 | 0.0477 | 0.0040 | 0.0180 | 0.0896 | 0.0000 | 0.0000 | 0.1051 | 0.2483 | 0.4373 |

TABLE E11

Base Component to Five Pseudocomponent Transformation Matrix

|   | C1 | CO2 | C2 | C3 | C4 | C5 | C6 | C7.1 | C7.2 | C7.3 | C7.4 | C7.5 | C7.6 |
|---|---|---|---|---|---|---|---|---|---|---|---|---|---|
| 1 | 1.0622 | −0.0008 | 0.0059 | −0.0013 | 0.0032 | 0.0127 | 0.0065 | 0.0087 | −0.0122 | −0.0028 | 0.0035 | 0.0018 | −0.0044 |
| 2 | −0.0273 | 0.0487 | 0.0617 | 0.0790 | 0.1084 | 0.1773 | 0.2062 | 1.1058 | 1.1002 | 0.1779 | −0.0878 | −0.1413 | −0.1558 |
| 3 | −0.0051 | −0.0600 | 0.1282 | 0.1090 | 0.0969 | 0.1176 | 0.0142 | −0.0762 | 0.1473 | 1.5062 | 0.7121 | 0.1730 | −0.2790 |
| 4 | −0.0012 | 1.2137 | 0.4953 | 0.2423 | 0.0794 | −0.0467 | −0.0266 | −0.0599 | 0.0304 | −0.0451 | −0.0573 | −0.0370 | 0.0060 |
| 5 | −0.0095 | 0.0093 | 0.0068 | 0.1125 | 0.1415 | −0.0289 | 0.0395 | 0.2186 | −0.1498 | −0.3240 | 0.2460 | 0.8793 | 1.6566 |

TABLE E12

Five Pseudocomponent to Three Pseudocomponent Transformation Matrix

|   | 1 | 2 | 3 | 4 | 5 |
|---|---|---|---|---|---|
| 1 | 1.1773 | 0.0040 | −0.0301 | 0.1349 | −0.0256 |
| 2 | 0.0067 | 0.4758 | 0.0289 | −0.0324 | −0.0156 |
| 3 | −0.1330 | 0.4465 | 1.2184 | 0.6519 | 0.9249 |

TABLE E13

Three Pseudocomponent to Five Pseudocomponent Transformation Matrix

|   | 1 | 2 | 3 |
|---|---|---|---|
| 1 | 0.8294 | 0.0000 | 0.0000 |
| 2 | 0.0000 | 2.0592 | 0.0000 |
| 3 | 0.0000 | 0.0000 | 0.4151 |
| 4 | 0.1741 | −0.2205 | 0.1711 |
| 5 | −0.0035 | −0.8386 | 0.4138 |

SYMBOLS

A, Matrix used in equation of state computations; elements are defined in Eq. (15)

$\alpha$, Quantity used in equation of state computations; defined in Eqs. (18) and (22)

$\alpha$, Linear multiplier used in Eq. (4), (5), (6), (8), (9), and (10)

$A_i$, Modification of matrix A for i pseudocomponents; defined in Eq. (26)

$A_{ii}$, Modification of matrix A for i pseudocomponents; defined in Eq. (24)

B, Vector used in equation of state computations b, Quantity used in equation of state computations; defined in Eqs. (19) and (23)

$b_k$, Parameter used in equation of state computations d, In Eq. (3), denotes dominant component e, Base of the natural logarithm m, Vector of component masses, typically expressed as mass-moles $m_1$, Equation of state parameter, the value of which depends on the equation of state being used $m_2$, Equation of state parameter, the value of which depends on the equation of state being used P, Matrix containing pseudocomponent vectors Pr, Reduced pressure $T_r$, Reduced temperature v, Entry in singular vector x, In Eq. (3), denotes non-zero term other than dominant component x, Concentration or vector of concentrations, typically expressed as mole fraction Z, Compressibility factor $\alpha$, Parameter used in equation of state computations $\delta$, Equation of state interaction parameter $\Psi$, Vector of fugacity coefficients

SUBSCRIPTS b, Denotes base component or base component representation c, Denotes a component d, Denotes a dominant component i, Denotes number of pseudocomponents used j, Denotes number of pseudocomponents used k, Denotes a component l, In eq. (15), denotes a component l, In Eq. (7), (8), (9), and (10), denotes a particular lumped pseudocomponent.

n, Denotes a particular lumped pseudocomponent o, Denotes an observed concentration p, Denotes a pseudocomponent q, Denotes a pseudocomponent

What is claimed is:

1. A method for estimating one or more properties of a multi-component fluid contained in one or more volumetric zones, comprising the steps of:
    (a) characterizing the multi-component fluid using a set of base components;
    (b) defining a set of fluid compositions corresponding to fluid compositions predicted to occur in one or more volumetric zones;
    (c) developing a fluid characterization of the multi-component fluid using one or more pseudocomponents by a sequence of steps comprising:
        (i) defining an ordered set of vectors corresponding to a characteristic of said base components, each vector containing one entry for each base component, the first vector of the ordered set being most representative of the set of compositions according to a predetermined criterion and each vector thereafter in the ordered set being less representative of the set of compositions than the vector before it;
        (ii) selecting a subset of said ordered set of vectors, said subset comprising the first vector and a predetermined number of vectors immediately thereafter;
        (iii) defining a set of pseudocomponents based on said subset of vectors; and
    (d) using the fluid characterization to predict one or more properties of said multi-component fluid.

2. The process of claim 1 wherein sub-step (iii) of defining a set of pseudocomponents based on said subset of vectors, comprises the steps of (1) for each vector of the subset of vectors, determining a dominant component corresponding to a predetermined criterion, and (2) determining a pseudocomponent corresponding to each said dominant component.

3. The process of claim 2 wherein step (2) comprises determining a set of vectors of linear multipliers using least squares minimization and then normalizing each vector in said set of vectors.

4. The process of claim 2 wherein step (2) comprises modifying each selected vector by eliminating all other selected vectors' dominant components and normalizing each modified vector.

5. The process of claim 4 further comprising using the resulting pseudocomponents to determine representations of fluid compositions in terms of said pseudocomponents and computing a property of each pseudocomponent as being equivalent to a corresponding property of the pseudocomponent's dominant component.

6. The method of claim 5 further comprising computing each pseudocomponent's fugacity, equilibrium ratio, or other physical quantity controlling phase equilibrium as being equal to the fugacity, equilibrium ratio, or other physical quantity controlling phase equilibrium of its dominant component.

7. The method of claim 6 further comprising performing phase behavior computations based on the pseudocomponents' fugacities, equilibrium ratios, or other physical quantities controlling phase equilibrium.

8. The process of claim 1 wherein the multi-component fluid comprises base components comprising methane, ethane, propane, butane, and heavier hydrocarbons.

9. The process of claim 8 wherein base components further comprise carbon dioxide, nitrogen, and hydrogen sulfide.

10. The process of claim 1 wherein the number of fluid compositions in step (b) exceeds the number of base components.

11. The process of claim 1 wherein the number of base components ranges from 10 to 50 and the subset of vectors ranges from 3 to 10.

12. The process of claim 1 wherein the volumetric zones comprise flowlines and processing facilities.

13. The process of claim 1 wherein the volumetric zones comprise flowlines and processing facilities of a chemical plant.

14. The process of claim 1 wherein the volumetric zone comprises at least a portion of a hydrocarbon-bearing formation.

15. The process of claim 7 further comprising determining the phase behavior of fluid in a volumetric zone.

16. The method of claim 1 wherein the fluid characterizations, in terms of either the base components and one or more sets of pseudocomponents or in terms of two or more sets of pseudocomponents, are used in different computational regions, further comprising the steps of:

(a) defining computational regions comprising the volumetric zones within a petroleum reservoir, wells and surface flow lines used in the production of petroleum, surface facilities and groups of surface facilities related to production and subsequent processing of petroleum;

(b) specifying which fluid characterization is to be used within each computational region;

(c) identifying instances where fluids flow between computational regions using different fluid characterizations; and (d) transforming the fluids flowing between computational regions from their original representations to the representations used in the computational regions into which they are flowing.

17. A method for estimating one or more properties of a multi-component fluid contained in a volumetric zone, comprising the steps of:

(a) characterizing the multi-component fluid using a set of base components;

(b) defining a set of fluid compositions corresponding to fluid compositions predicted to occur in the volumetric zone;

(c) characterizing the multi-component fluid using one or more pseudocomponents by a sequence of steps comprising:

(i) defining an ordered set of vectors corresponding to a characteristic of said base components, each vector containing one entry for each base component, the first vector of the ordered set being most representative of the set of compositions according to a predetermined criterion and each vector thereafter in the order being less representative of the set of compositions than the vector before it;

(ii) selecting a subset of said ordered set of vectors, said subset comprising the first vector and a predetermined number of vectors immediately thereafter;

(iii) for each selected vector, determining a dominant component corresponding to a predetermined criterion;

(iv) determining a pseudocomponent corresponding to each said dominant component;

(d) using the fluid characterization to predict one or more properties of said multi-component fluid.

18. The method of claim 17 wherein sub-step (iv) of step (c) comprises modifying each selected vector by eliminating all other selected vectors' dominant components and normalizing each modified vector.

19. The method of claim 17 wherein sub-step (iv) of step (c) comprises determining a set of vectors of linear multipliers using least squares minimization and then normalizing each vector in said set of vectors.

20. A method for performing computations involving a multi-component fluid mixture by representing the mixture as a set of pseudocomponents, said method comprising (a) characterizing the fluid mixture using a set of base components;

(b) identifying a set of compositions representative of those compositions expected to be encountered in the computations of interest, said set containing more compositions than there are base components;

(c) determining an ordered set of vectors, the number of vectors in the set being equal to the number of base components, with each vector containing one entry for each base component, such that the first vector reproduces the set of representative compositions as accurately as any single vector can, the first and second vectors combined reproduce the set of representative compositions as accurately as any two vectors combined can, the first three vectors combined reproduce the set of representative compositions as accurately as any three vectors combined can, and so on up through the number of vectors in the set;

(c) deciding upon a certain number of these vectors to be retained for subsequent computations;

(d) retaining the specific vectors that are the first of this number in the ordered set of vectors;

(e) for each retained vector, determining a dominant component that is most representative of the vector's partitioning between phases;

(f) modifying each retained vector by eliminating from it all other retained vectors' dominant components;

(g) normalizing each retained vector so modified by scaling its remaining components such that they sum to one;

(h) using the resulting normalized vectors as pseudocomponents;

(i) determining characterizations of fluid compositions in terms of these pseudocomponents;

(j) computing each pseudocomponent's fugacity, equilibrium ratio, or other physical quantity controlling phase equilibrium as being equal to the fugacity, equilibrium ratio, or other physical quantity controlling phase equilibrium of its dominant component; and (k) performing phase behavior computations based on the fugacities, equilibrium ratios, or other physical quantities controlling phase equilibrium so defined.

21. The method of claim 20 further comprising the step of performing compositional simulation of a volumetric zone for a series of time steps.

22. A method for estimating over a time step one or more properties of a multi-component fluid contained in both a first volumetric region and a second volumetric region, each region comprising a plurality of volume cells arranged adjacent to one another, and the regions having a boundary therebetween which is crossed by at least a fraction of the fluid over the time step, comprising the steps of:

(a) characterizing the multi-component fluid for both regions using a set of base components;

(b) defining a set of fluid compositions corresponding to fluid compositions predicted to occur in both regions;

(c) characterizing the multi-component fluid in the first region using one or more pseudocomponents by a sequence of steps comprising:

(i) defining an ordered set of vectors corresponding to a characteristic of said base components, each vector containing one entry for each base component, the first vector of the ordered set being most representative of the set of compositions in the first region according to a predetermined criterion and each vector thereafter in the ordered set being less representative of the set of compositions in the first region than the vector before it;

(ii) selecting a subset of said ordered set of vectors, said subset comprising the first vector and a predetermined number of vectors immediately thereafter, said subset of vectors corresponding to a pseudocomponent characterization of the multi-component fluid in the first region;

(d) characterizing the multi-component fluid in the second region using one or more pseudocomponents by performing the sequence of steps of step (c) with respect to the second region;

(e) transforming the fraction of the multi-component fluid that crosses the boundary over the time step by the steps of transforming the pseudocomponent characterization of the multi-component fluid in the first region to a base component characterization of the multi-component fluid and transforming the base characterization to the second pseudocomponent characterization;

(f) performing a compositional simulation using the first pseudocomponent characterization to predict one or more properties of said multi-component fluid in the first region and using the second pseudocomponent characterization to predict one or more properties of said multi-component fluid in the second region.

* * * * *